US008945514B2

(12) United States Patent
Hasserodt

(10) Patent No.: US 8,945,514 B2
(45) Date of Patent: Feb. 3, 2015

(54) CONTRAST AGENTS FOR MAGNETIC RESONANCE IMAGING

(75) Inventor: Jens Hasserodt, Lyons (FR)

(73) Assignees: Centre National de la Recherche Scientifique, Paris (FR); Ecole Normale Superieure de Lyon, Lyons (FR)

( * ) Notice: Subject to any disclaimer, the term of this patent is extended or adjusted under 35 U.S.C. 154(b) by 2353 days.

(21) Appl. No.: 11/547,088

(22) PCT Filed: Mar. 31, 2005

(86) PCT No.: PCT/FR2005/000784
§ 371 (c)(1),
(2), (4) Date: Sep. 29, 2006

(87) PCT Pub. No.: WO2005/094903
PCT Pub. Date: Oct. 13, 2005

(65) Prior Publication Data
US 2007/0218010 A1 Sep. 20, 2007

(30) Foreign Application Priority Data
Mar. 31, 2004 (FR) ..................................... 04 03389

(51) Int. Cl.
A61K 49/00 (2006.01)
A61B 5/055 (2006.01)
A61K 49/12 (2006.01)
C07D 225/00 (2006.01)
A61K 49/10 (2006.01)
A61K 49/08 (2006.01)
C07D 401/14 (2006.01)

(52) U.S. Cl.
CPC ............ A61K 49/106 (2013.01); A61K 49/085 (2013.01); A61K 49/10 (2013.01); C07D 401/14 (2013.01)
USPC ....................................... 424/9.363; 540/465

(58) Field of Classification Search
None
See application file for complete search history.

(56) References Cited

U.S. PATENT DOCUMENTS 5,707,605 A 1/1998 Meade et al.
6,432,900 B1 * 8/2002 Appel et al. ................... 510/376
7,625,930 B2 * 12/2009 Hovinen et al. ............... 514/332

FOREIGN PATENT DOCUMENTS

WO WO 9736619 A2 * 10/1997

OTHER PUBLICATIONS

Cryle, M.J., et al., "Carbon-carbon bond cleavage by cytochrome-P450Biol . . . ", 2004, Chemical Communications, pp. 86-87.*
Rautio et al. Nature Reviews Drug Discovery 2008, 7, pp. 255-270.*
Wang et al. Drug Delivery: Principles and Applications, 2005 John Wiley & Sons, Inc. Publication, Section 8.3, pp. 136-137.*
Smith, D. A. Current Opinion in Drug Discovery & Development 2007, 10, 550-559.*
Testa, B. Current Opinion in Chemical Biology 2009, 13, pp. 338-344.*
Wieghardt, K., et al., "Synthesis, Properties, and Electrochemistry of Transition Metal . . . ", 1986, Inorganic Chemistry, 25, pp. 4877-4883.*
Stavila, V., et al., "Effective Repression of the Fragmentation . . . ", 2008, Eur. J. Organicl Chemicstry, 25, pp. 3943-3947.*
Wieghardt et al., "Syntheses, Properties, and Electrochemistry of Transition-Metal Complexes of the Macrocycle 1,4,7-Tris(2-pyridylmethyl)-1,4,7-triazacyclononane (L). Crystal Structures of [NiL](ClO$_4$)$_2$, [MnL](ClO$_4$)$_2$, and [PdL](PF$_6$)$_2$ Containing a Distorted-Square-Base-Pyramidal Pd$^{II}$N$_5$ Core", Inorganic Chemistry, American Chemical Society, vol. 25, No. 27, pp. 4877-4883, 1986.
Christiansen et al., "Synthesis and Structure of Metal Complexes of Triaza Macrocycles with Three Pendant Pyridylmethyl Arms", Inorganic Chemistry, vol. 25, No. 16, pp. 2813-2818, 1986.
Tsukube et al., "Triazamacrocycle Having Pyridine-Pendant Arms as a New Na+ Ion-Selective Ionophore", vol. 30, No. 30, pp. 3983-3986, 1989.
International Search Report dated Oct. 7, 2005.
Anne Bourry et al. "Studies on Pyrrolidinones: Some Attempts to Improve the Synthesis of Methyl N-(3,4,4',5-Tetramethoxybenzhydryl)pyroglutamate (HEI 81) by Using N-Acyl Iminium Salts Methodologies" Journal of Heterocyclic Chemistry (2002) 39, 109-118.
Alan R. Katritzky et al., The Chemistry of N-Substituted Benzotriazoles; Part II. The Preparation of Tertiary Amines Containing Tertiary-alkyl Groups from Ketones, Secondary Amines, and Organometallic Reagents Synthesis (1989) 66-69.
Alan R. Katritzky et al., "Properties and Synthetic Utility of N-Substituted Benzotriazoles" Chem. Rev. (1998) 98:409-548.
Alan R. Katritzky et al., "Amino(hetero)arylmethylation of Phenols with N-[α-Amino(hetero)arylmethyl]benzotriazoles" J. Org. Chem. (1999) 64, 6071-6075.
K. Niedenzu and K. R. Woodrum "Triazaboles and Related Triazole Derivatives of Boron" Inorg. Chem. (1989) 28, 4022-4026.
P.B. Rasmussen et al., "Studies on Organophosphorus Compounds XLIX* an Improved Method for the Preparation of 2,5-disubstituted 1,3,4-thiadiazoles and 1,3,4-thiadiazole-2(3H)-thiones**" (*) Part XLVII. N. M. Yousif, U. Pedersen, B. Yde, and S.O. Lawesson, Tetradron (1984), 40: 2663; (**) Preliminary communication in Chem. Lett. Japan, (1983) p. 809.
Emily E. Weinert et al., "Substituents on Quinone Methides Strongly Modulate Formation and Stability of Their Nucleophilic Adducts" J. Am. Chem. Soc. (2006)n 128, 11940-11947.
Emily E. Weinert et al. "Substituents on Quinone Methides Strongly Modulate Formation and Stability of Their Nucleophilic Adducts" J. Am. Chem. Soc. (2006) 128:11940-11947, American Chemical Society.

* cited by examiner

Primary Examiner — Michael G Hartley
Assistant Examiner — Lance Rider
(74) Attorney, Agent, or Firm — Buchanan Ingersoll & Rooney PC

(57) ABSTRACT

The invention relates to contrast agents for magnetic resonance imaging comprising a chelating ligand and a transition metal ion, said ligand carrying a substituent capable of reacting chemically or biochemically with a target substance while bringing about a change in the spin state.

18 Claims, No Drawings

CONTRAST AGENTS FOR MAGNETIC RESONANCE IMAGING

The present invention relates to contrast agents for magnetic resonance imaging.

BACKGROUND OF THE INVENTION

Magnetic resonance imaging (MRI) is a technique widely used in the medical field, in particular for diagnostic purposes. MRI is based mainly on the observation of the magnetization of the spins of the nuclei of hydrogen atoms in water molecules. It consists in measuring the relaxation by two modes (T1 and T2) of the water molecules with respect to a distribution at equilibrium, in order to form an image. The relaxation occurs after a state in which all the spins have been completely aligned under the effect of an external magnetic field by use of a radiofrequency pulse. MRI makes it possible to distinguish between the regions of high concentration and the regions of low concentration of a contrast agent. In the biological field, the image obtained reveals the tissues rich in contrast agent, essentially those which are hydrophilic in nature.

First-generation contrast agents are "passive" agents which are distributed through the sample subjected to MRI, essentially as a function of lipophilicity gradients and non-specific bonds.

Studies have been carried out to define active agents, that is to say agents capable of revealing the presence of a chemical or biochemical activity, pH conditions or a concentration of a specific ion. These agents are composed of a strongly paramagnetic ion complexed by a ligand, the ion generally being Gd(III). The contrast agents comprising such a strongly paramagnetic ion consequently constitute a permanent molecular magnet which always has a greater or lesser effect on the relaxation of the surrounding water molecules. The means for rendering these complexes of permanent molecular magnet type sensitive to specific chemical compounds of their environment was based essentially on the modification of the accessibility of the immediate environment of the paramagnetic metal for water molecules. Such labels, for which the relaxation by an enzymatic activity is improved in that they act as catalysts for the rapid exchange of water molecules are described in various documents.

U.S. Pat. No. 5,707,605 discloses an MRI agent which is a complex of a paramagnetic metal ion and of a ligand, said ligand comprising a chelating group and a substituent which is covalently bonded to the chelating group. In the absence of target substance, the substituent is combined with or bonded to the metal ion of the complex and it occupies or blocks at least one coordination site of the metal ion. All the coordination sites of the metal ion are then saturated by the chelating group and the substituent. In the presence of the target substance, the substituent reacts with said substance and ceases to block or to occupy at least one coordination site of the metal ion, so that a rapid exchange of water can take place on the site, which improves the MR image. A derivative of 1,4,7,10-tetraazacyclododecane-N,N',N'',N'''-tetraacetic acid (DOTA) in which one of the acetate substituents is replaced by a hydroxyethyl β-galactose substituent is an example of such a complex. In this complex, the end group sensitive to the enzyme has only a slight protective effect on the metal center with regard to coordination by water: the mean number of water molecules which are coordinated at any moment to the $9^{th}$ coordination site of the gadolinium is 0.65 instead of 1.02 for the "cleaved" form of a similar compound comprising a ligand capable of occupying only 8 coordination sites (Cf. Meade, T. J. et al., "In vivo visualization of gene expression using magnetic resonance imaging. Nature Biotechnology, 18, 321-325 (2000)"). This low additional access of the water molecules during the bioactivation of the contrast agent does not satisfactorily modify the relaxation.

In addition, the Applicant Company has discovered another disadvantage related to this contrast agent, namely that the latter does not react with a sufficient speed with the target substance, namely the enzyme β-galactosidase. This is because the Applicant has carried out experiments which have shown that coinjection of this same contrast agent with the enzyme into a living test organism, namely zebra fish embryos, does not result in any modification in the contrast, neither after 24 hours nor after 48 hours. This result was obtained in comparison with an identical experiment in which the coinjected agent was a commercial chromogenic agent which gave rise to an intense coloring of the embryo related to its enzymatic conversion.

WO 99/21592 discloses the application of the technique of U.S. Pat. No. 5,707,605 to a target substance of the therapeutic agent type. The improvement in the degree of contrast which can be obtained using the labels of the type of those disclosed in the abovementioned documents is, however, limited.

Complexes formed by a transition metal ion and by a ligand which can exist in a high spin form and in a low spin form, depending on the nature of the ligand, are known. In the high spin state, virtually all the electrons are unpaired electrons; there is no internal compensation of their spins, which produces a substantial increase in the magnetic moment. In the low spin state, the complexes have a weak, indeed even zero, magnetic moment, depending on the number of unpaired electrons (generally 0 or 1). An example of Fe(II) compound complexed by a hexadentate macrocyclic ligand of low spin is given by Wieghardt et al. (Inorg. Chem., 1986, 25, 4877) and an example of an Fe(II) compound complexed by a similar pentadentate macrocyclic ligand of high spin is given by Spiccia et al. (Inorg. Chim. Acta, 1998, 279, 192).

SUMMARY OF THE INVENTION

The aim of the invention is to provide a contrast agent capable of detecting a target substance or the chemical activity associated with this target substance in a cell or a tissue subjected to MRI during the phase of acquisition and of construction of the image.

A contrast agent for MRI according to the present invention is a complex comprising a chelating ligand and a transition metal ion, said ligand carrying a substituent capable of reacting chemically or biochemically with a target substance while bringing about a change in the spin state, and having:
a) either the formula (I)

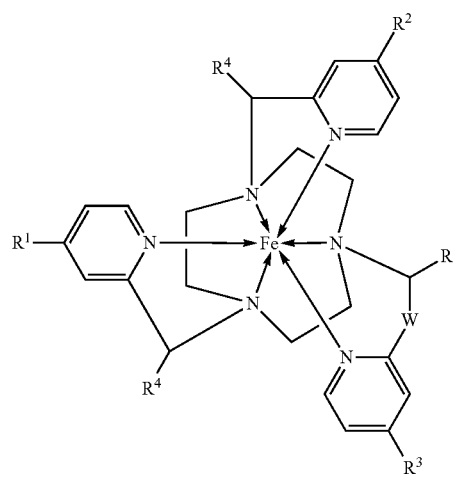

in which:
R⁴ represents a hydrogen atom or a linear or branched alkyl group of 1 to 4 carbon atoms or an aryl radical;
W represents a —(CH₂)$_m$— group, m being equal to 0 or to 1;
R⁵ represents a group capable of reacting with the target substance to sever the connection between the N atom of the macrocycle and the carbon carrying said group R⁵, or represents a hydrogen atom, it being understood that:
  i) when R⁵ represents a group capable of reacting with the target substance to sever the connection between the N atom of the macrocycle and the carbon carrying said group R⁵ (complexes Ia), R¹ to R³, denoted by R$^i$, represent, independently of one another, a hydrogen atom or a group chosen in order to adjust the properties of solubility and of dispersibility in biological media and of magnetic moment of the complex, it also being possible for one of the R$^i$ groups to represent a group capable of undergoing electronic modification of the neighboring pyridyl group by reaction with the target substance;
  ii) when R⁵ represents a hydrogen atom (complexes Ib), one of the R$^i$ groups represents a group capable of undergoing electronic modification of the neighboring pyridyl group by reaction with the target substance, it being possible for the remaining R$^i$ groups to represent, independently of one another, a hydrogen atom or to be chosen in order to adjust the properties of solubility and of dispersibility in biological media and of magnetic moment of the complex;
b) or the formula (II)

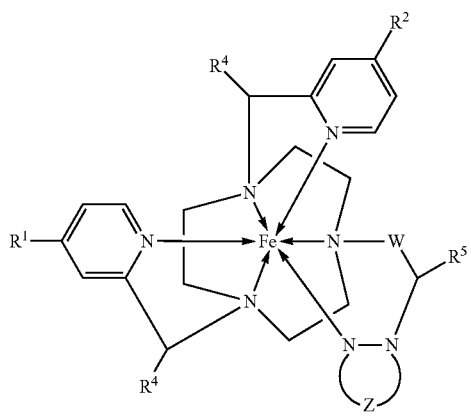

in which:
R¹ and R², denoted by R$^i$, represent, independently of one another, a hydrogen atom or a group chosen in order to adjust the properties of solubility and of dispersibility in biological media and of magnetic moment of the complex;
R⁴ and W are as defined above;
R⁵ represents a group (—C₆X₄—Y—R⁶) in which X is an electron-withdrawing group, Y is a heteroatom chosen from an oxygen atom, a nitrogen atom or a sulfur atom, and R⁶ represents a β-galactosyl group or a β-glucuronyl group capable of undergoing cleavage by a glycosidase, or an aminoacyl group (for example, an L-prolyl or L-leucyl group) capable of undergoing cleavage by an aminopeptidase, or an acyl group, such as —COC₅H₁₁, capable of undergoing cleavage by an esterase or a lipase, or a group capable of undergoing a retrograde aldol reaction with a natural aldolase, for example a group of α,β-dihydroxyketone type

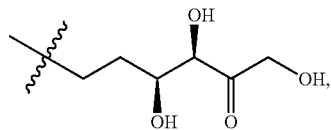

or a phosphoryl group capable of undergoing conversion by a phosphatase;
Z is a divalent group which forms, with the two nitrogen atoms which carry it, an aromatic benzotriazole, triazole, tetrazole or pyrazole ring, it being possible for said aromatic ring to carry an NO₂ substituent.

DETAILED DESCRIPTION OF THE PREFERRED EMBODIMENTS

In a compound (II), the X groups can represent, independently of one another, a hydrogen atom, a fluorine atom or an NO₂ group.

The R⁴ groups are chosen in order to increase the stiffness of the ligand and consequently to increase the stability of the initial metal complex and of the final complex after conversion by the target substance.

The choice of the W group is made in order to refine the rate of self-collapse.

The change in the spin state is obtained by the removal or by the electronic modification of a substituent.

When the removal of a substituent is concerned, the change in spin is the passage from a low spin (diamagnetic complex inactive in MR) to a high spin (paramagnetic complex active in MR).

When the electronic modification of a substituent is concerned, the change in spin is generally the passage from a low spin to a high spin. However, a change in the opposite direction can also be obtained by the choice of an appropriate ligand.

The transition metal of the compound of formula (I) or (II) is iron, for which a change in the oxidation state from II to III is preferable. This is because high-spin iron(III) is recognized for its high power, in comparison with high-spin iron(II), to modify the relaxation of the neighboring protons by virtue of its higher electronic relaxation time $\tau_s$: $10^{-9}$-$10^{-11}$ s (high-spin Fe(III)); $10^{-12}$-$10^{-13}$ S (high-spin Fe(II))(see the publications by I. Bertini, C. Luchinat, G. Parigi: "Solution NMR of Paramagnetic Molecules", *Current Methods in Inorganic Chemistry*, Vol. 2, Elsevier, Amsterdam, 2001; and R. B. Lauffer, Chem. Rev., 1987, 87, 901). Compounds based on high-spin Fe(II) often have a tendency to be oxidized in order to achieve the d⁵ electronic state of iron(III), which constitutes a very stable state by virtue of a half-filled d electron shell. In contrast, an iron(III) surrounded by a multidentate ligand providing a strong field, as is the case in this invention, results in all 6 of its electrons being placed in the paired state in low energy d orbitals (3 degenerate orbitals of t₂g type), which stabilizes this oxidation state as there is no possibility of removing a high energy electron during the oxidation, as is the case for high-spin iron(II). It is thus a considerable advantage of this invention to start from a tracer stable to oxidation and without electron spin to arrive, after enzymatic initiation, at a high spin complex having an electronic relaxation time favorable to NMR imaging. The electron spin of the high-spin iron(III) "communicates well" with the nuclear spin of a proton.

In the context of the present invention
a halogen atom means a chlorine, fluorine, bromine or iodine atom. Generally, the chlorine atom and the fluorine atom are preferred;
a "5- or 6-membered aromatic ring" means an optionally heterocyclic group chosen from a phenyl, pyridyl, pyrimidinyl, pyrazinyl, indolyl, indazolyl, furyl and thienyl group and their derivatives carrying various substituents chosen from the methyl, chloro, fluoro, nitro, methoxy, carboxy and acetamido groups;
a "5- or 6-membered aliphatic ring" means a cyclohexyl group or a cyclopentyl group;
an "alkyl" group means a linear or branched aliphatic chain of 1 to 4 carbon atoms;
an "aryl radical" means a group comprising one or more condensed or noncondensed aromatic nuclei.

According to a first embodiment of the complexes of formula I, the $R^5$ substituent is a group capable of reacting with the target substance to sever the connection between the N atom of the macrocycle and the carbon carrying said $R^5$ group. These specific complexes are denoted by Ia.

In the Ia complexes, the $R^i$ groups represent, independently of one another, a hydrogen atom, an electron-withdrawing group chosen from the —$COOR^7$ group, the —$NO_2$ group and a halogen atom, in order to control the spin state of the metal, or a group carrying negative charges, such as the —$CH_2$—$COO^-$ group, in order to compensate for the two positive charges of the iron(II) and thus to render the agent neutral overall.

One of the three $R^i$ groups can additionally represent a —$CH(OH)CH(COOH)NH_2$ group, the remaining $R^i$ groups then being as defined above.

$R^7$ can represent an alkyl group having from 1 to 4 carbon atoms. Such an $R^7$ group can be of use in reducing the polarity of the whole agent.

According to a first alternative form of the Ia complexes, hereinafter denoted by Ia-1, $R^5$ can be represented by the formula -E-$R^6$ in which $R^6$ is as defined above and E is a spacer group capable of self-collapsing in the event of the E-$R^6$ bond being cut. $R^6$ is capable of reacting with a chemical compound or a biochemical compound, triggering a series of cleavages resulting in the elimination of the pyridine-2-carbaldehyde according to the mechanism set out in the description below.

E can be an —O—CO—(CR'$_2$)$_n$—Y— group in which:
the R' groups represent, independently of one another, a hydrogen atom or a group chosen to prearrange the spacer in order to accelerate its self-collapse after cleavage of the $R^6$. More particularly, the R' groups can represent a methyl group or two R' groups carried by two neighboring carbon atoms together form a 5- or 6-membered aliphatic or aromatic ring carried by the two neighboring carbon atoms (see, for example: L. A. Carpino., J. Org. Chem., 1989, 54, 3303);
n is an integer equal to 3 or 4,
Y is a heteroatom chosen from an oxygen atom, a nitrogen atom or a sulfur atom.

The 5- or 6-membered aromatic ring formed by two R' groups can be chosen from the phenyl, pyridyl, pyrimidinyl, pyrazinyl, indolyle, indazolyl, furyl and thienyl groups, it being possible for said groups to carry various substituents chosen from the methyl, chloro, fluoro, nitro, methoxy, carboxyl and acetamido groups. The 5- or 6-membered aliphatic ring formed by two R' groups can be a cyclohexyl group or a cyclopentyl group.

Mention may be made, as example of E group in a compound Ia-1, of the following groups:

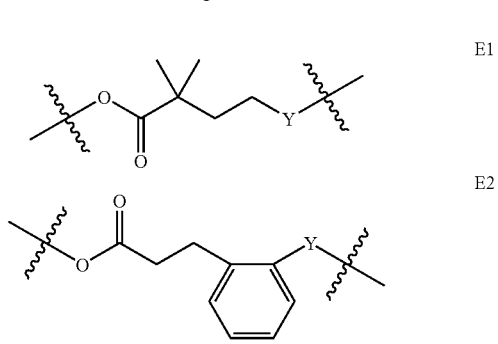

In an Ia-1 compound, the elimination of the pyridine-2-carbaldehyde forms a complex having a pentadentate ligand which changes the spin state of the complex and at the same time makes possible the attachment of a water molecule to a coordination site of the iron.

According to a second alternative form of the Ia complexes, hereinafter denoted by Ia-2, $R^5$ can be represented by a $C_6X_4$—Y—$R^6$ group in which ($C_6X_4$—Y) is a spacer group capable of self-collapsing in the event of the ($C_6X_4$—Y)—$R^6$ bond being cut and $R^6$ is a group which reacts with a chemical compound or a biochemical compound while triggering a sequence of cleavages bringing about the elimination of a quinonemethide according to the mechanism set out in the description below.

More particularly, X, Y and $R^6$ have the meanings given above.

In an Ia-2 complex, the ($C_6X_4$—Y) group can take one of the following meanings:

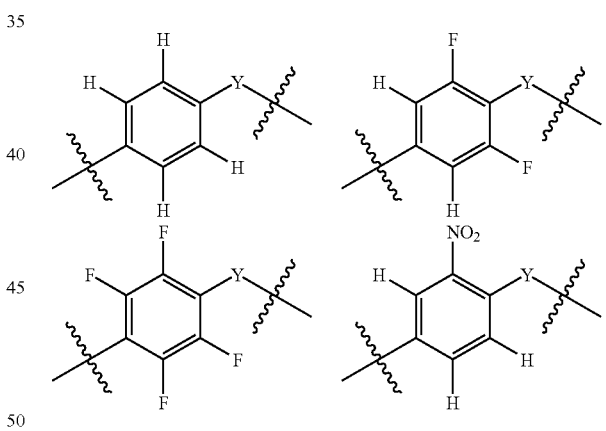

The elimination of the quinonemethide forms a complex having a pentadentate ligand which changes the spin state of the complex and at the same time makes possible the attachment of a water molecule to a coordination site of the iron.

According to a second embodiment of the complexes of formula I, the $R^5$ substituent represents a hydrogen atom. These complexes are denoted hereinafter by Ib.

In the Ib complexes, one of the $R^i$ groups represents a group capable of undergoing electronic modification of the neighboring pyridyl group by reaction with the target substance, for example a —$CH(OH)CH(COOH)NH_2$ group, and the remaining $R^i$ groups can represent, independently of one another, a hydrogen atom, a halogen atom or a group chosen from the —$COOR^7$ groups in which $R^7$ can represent an alkyl group having from 1 to 4 carbon atoms, the —$NO_2$ group or the —CHO group.

A complex of (Ib) type changes spin state under the effect of modification to one of the $R^i$ substituents. For example, an $R^i$ substituent of the —CH(OH)CH(COOH)NH$_2$ type rearranges under the action of L-threonine aldolase, producing a change in the spin state. No access is offered to a water molecule in the first coordination sphere during its conversion to —CHO according to the mechanism set out below. Only the water molecules of the second coordination sphere are influenced.

According to one embodiment of the complexes of general formula II, the X groups can represent, independently of one another, a hydrogen atom, a fluorine atom or an NO$_2$ group and the (C$_6$X$_4$—Y) group can take one of the following meanings:

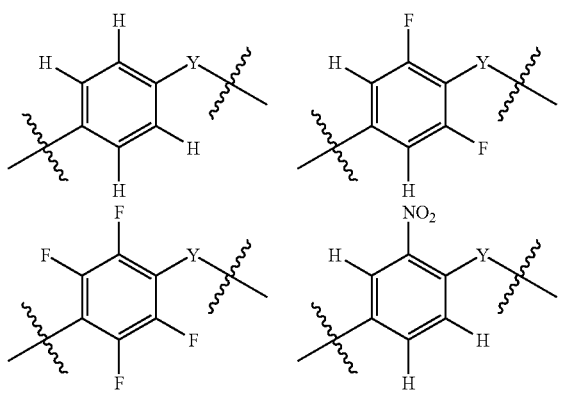

A complex according to the invention can be used as MRI label for detecting a target substance, such as, for example, an enzyme.

The action of a complex of the (Ia-1) type is illustrated by the reaction scheme (scheme 1) below for a complex in which $R^5$ is an -E-$R^6$ group, E is an —O—CO—C(CH$_3$)$_2$—(CH$_2$)$_2$—O— spacer group, $R^6$ is a β-galactosyl group, the $R^4$ groups represent hydrogen atoms and W is a single bond (in other words, m=0). This type of complex makes possible the detection of β-galactosidase. When the complex (Ia-1) is brought into the presence of β-galactosidase, cleavage of the β-galactosyl group occurs with formation of β-galactose, followed by spontaneous cleavage of the spacer group, with formation of the lactone 4,4-dimethyldihydrofuran-2-one, followed by spontaneous cleavage between the carbon atom which carried the $R^5$ substituent and the nitrogen atom of the macrocycle, with formation of pyridine-2-carbaldehyde. A water molecule can then become attached to the coordination site released and the iron(II) center adopts the high-spin state. This compound spontaneously oxidizes to the oxidation state III to become a high-efficiency MRI contrast agent.

Scheme 1

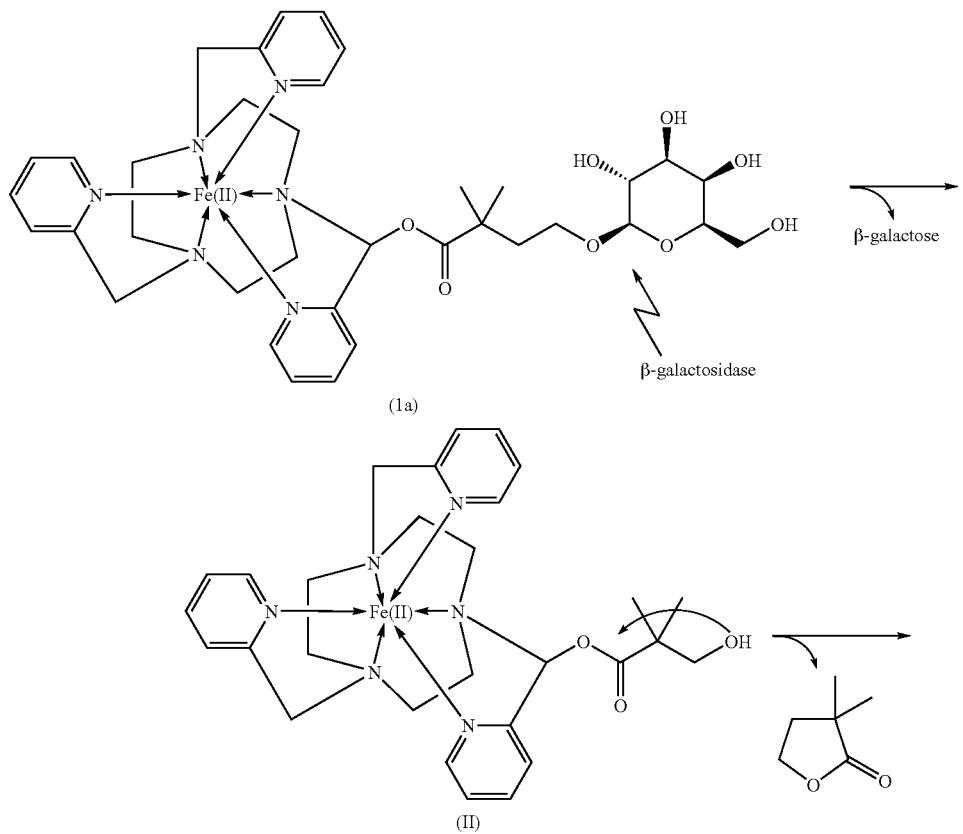

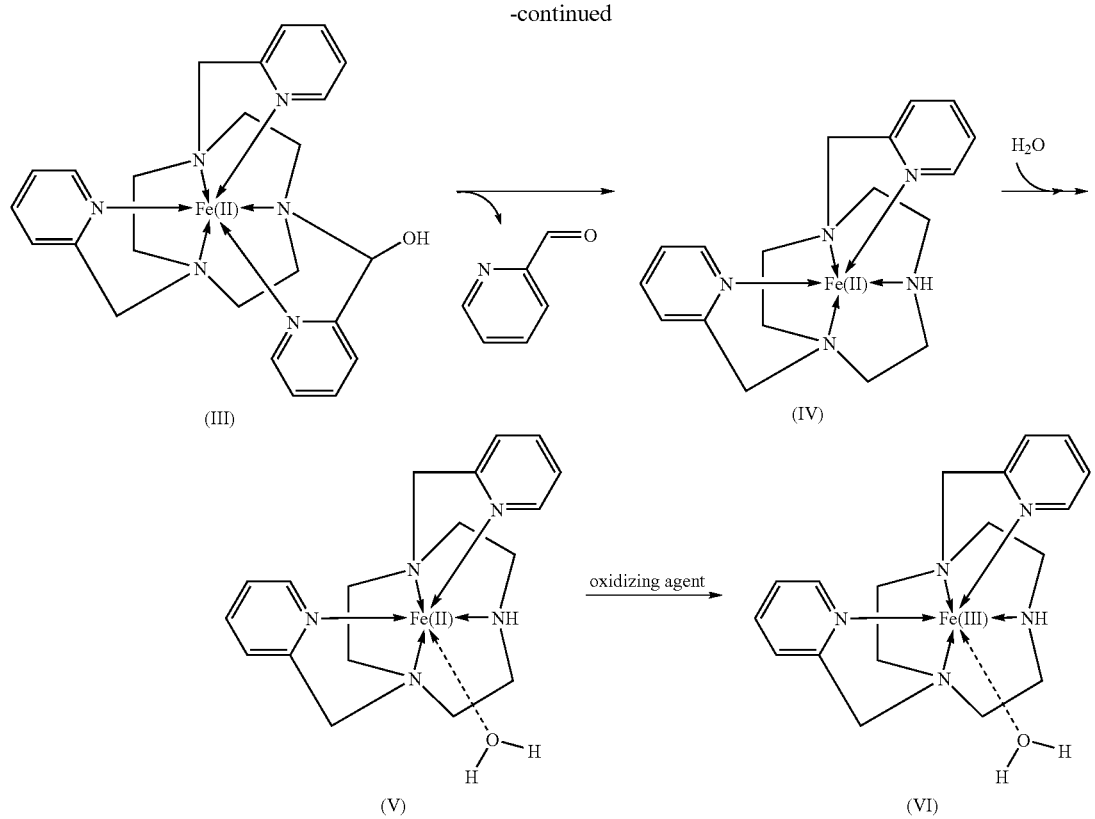

This technique makes it possible to detect, in addition to β-galactosidase, the presence of highly varied target substances. Examples of E-R$^6$ groups of use in detecting the presence of certain specific target substances or any other enzyme forming part of the categories to which the following target substances belong, in particular glycosidases, aminopeptidases, lipases and phosphatases, are reported below:

| E-R⁶ | Target substance |
|---|---|
| [structure: ester with hexanoate chain] | lipases (EC 3.1.1.3) |
| [structure with phenoxy and polyhydroxy ketone chain] | transaldolases (EC 2.2.1.2) (see, for example, E. Gonzalez-Garcia et al., Chem. Eur. J., 2003, 9, 893-899) |
| [structure with nitrophenyl prolyl amide] | prolyl aminopeptidase (EC 3.4.11.5) |
| [structure with aryl phosphate] | alkaline phosphatase (EC 3.1.3.1) |

The EC code is that used by the International Union of Biochemistry and Molecular Biology (IUBMB).

The meanings of the above examples can be found in databases, such as those listed in http://www.brenda.uni-koeln.de or http://au.expasy.org/enzyme/.

Likewise, the action of a complex of (Ia-2) type in which E is a spacer group (—$C_6X_4$—Y—) as defined above and $R^6$ is a β-galactosyl group is illustrated by reaction scheme 2 below.

When the complex (Ia-2) is brought into the presence of β-galactosidase, cleavage of the β-galactosyl group occurs with formation of β-galactose, followed by spontaneous cleavage between the carbon atom which carried the $R^5$ substituent and the nitrogen atom of the macrocycle, with the formation of quinonemethide. A water molecule can then become attached to the coordination site released and then the action of an oxidizing agent makes it possible to convert the iron(II) complex to the iron(III) complex.

Scheme 2

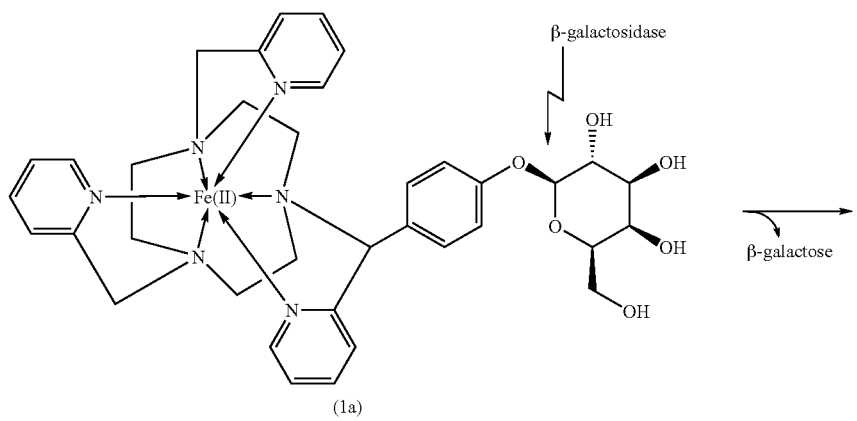

(1a)

-continued

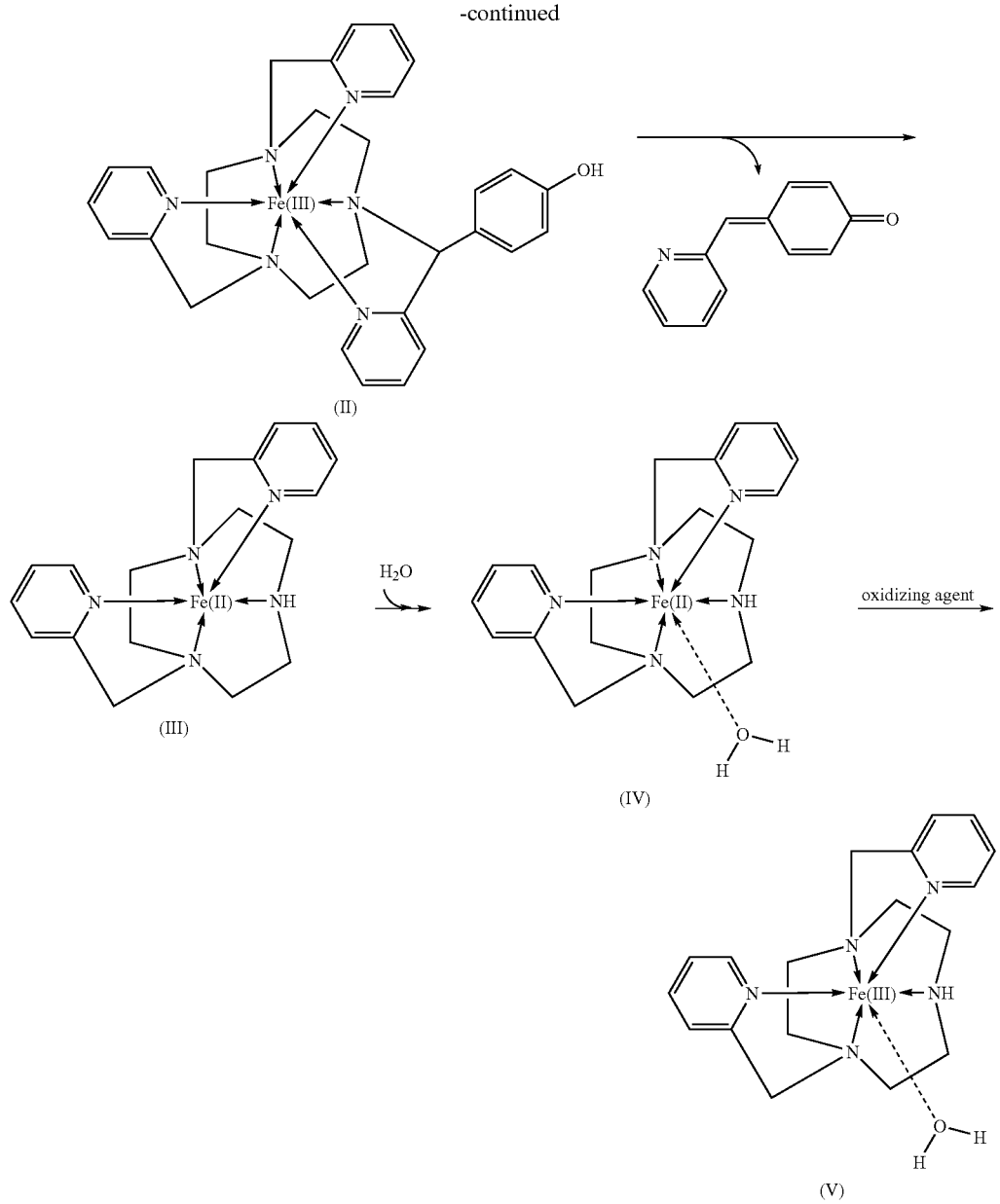

It is also possible in this case to detect, in addition to the β-galactosidase, the presence of highly varied target substances. Examples of $R^6$ groups of use in detecting the presence of certain specific target substances or any other enzyme forming part of the categories to which the following target substances belong, in particular glycosidases, aminopeptidases, lipases and phosphatases, are reported below:

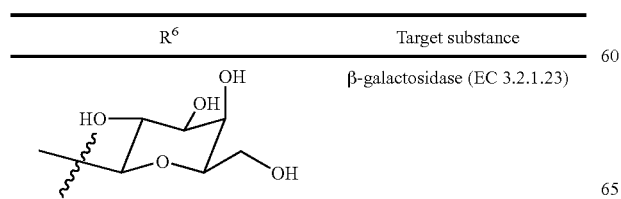

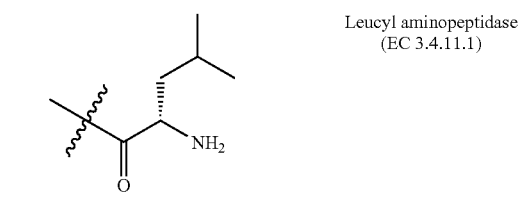

-continued

| $R^6$ | Target substance |
|---|---|
| 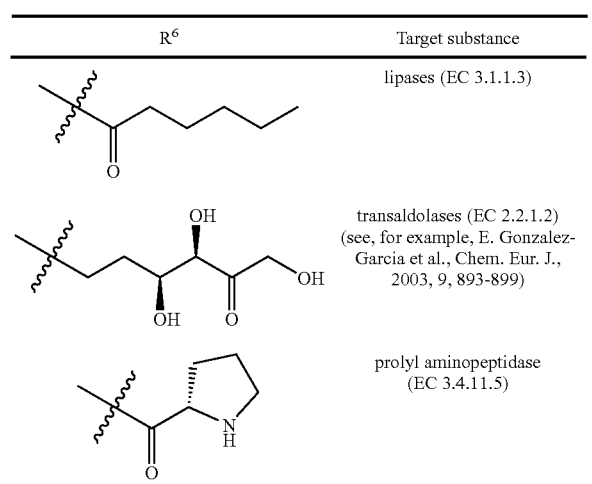 | lipases (EC 3.1.1.3) |
| | transaldolases (EC 2.2.1.2) (see, for example, E. Gonzalez-Garcia et al., Chem. Eur. J., 2003, 9, 893-899) |
| | prolyl aminopeptidase (EC 3.4.11.5) |

-continued

| $R^6$ | Target substance |
|---|---|
| 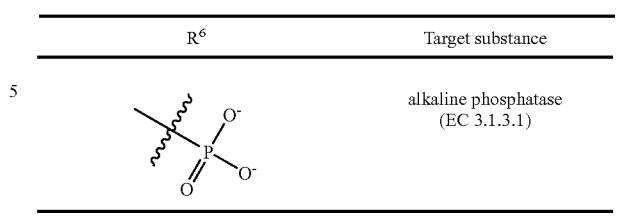 | alkaline phosphatase (EC 3.1.3.1) |

The action of a complex (Ib) which comprises an Fe ion and a ligand of the hexadentate type carrying an R substituent capable of undergoing electronic modification is illustrated by the reaction scheme below (scheme 3) for a complex in which one of the $R^i$ substituents is a —CH(OH)CH(COOH)NH$_2$ group and the other $R^i$ substituents are —NO$_2$ groups. Such a substituent rearranges under the action of L-threonine aldolase with the release of glycine, which brings about a change in spin state. It consequently makes it possible to detect L-threonine aldolase.

Scheme 3

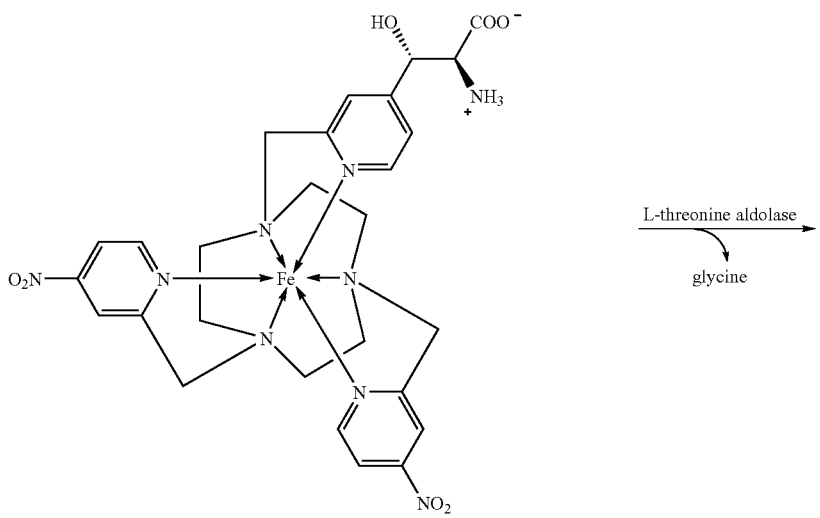

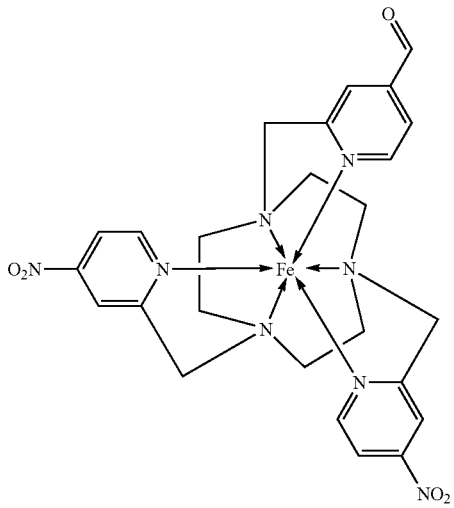

Likewise, the action of a complex of (II) type, in which E is a spacer group (—C$_6$X$_4$—Y—) as defined above, W is not a specific group (m=0) and R$^6$ is a β-galactosyl group, is illustrated by reaction scheme 4 below.

When the complex (II) is brought into the presence of β-galactosidase, cleavage of the β-galactosyl group occurs with formation of β-galactose, followed by a rearrangement of the spacer group so as to form a quinonemethide, which leads to the elimination of the benzotriazole group. A water molecule can then become attached to the coordination site released and then the action of an oxidizing agent makes it possible to convert the iron(II) complex to the iron(III) complex.

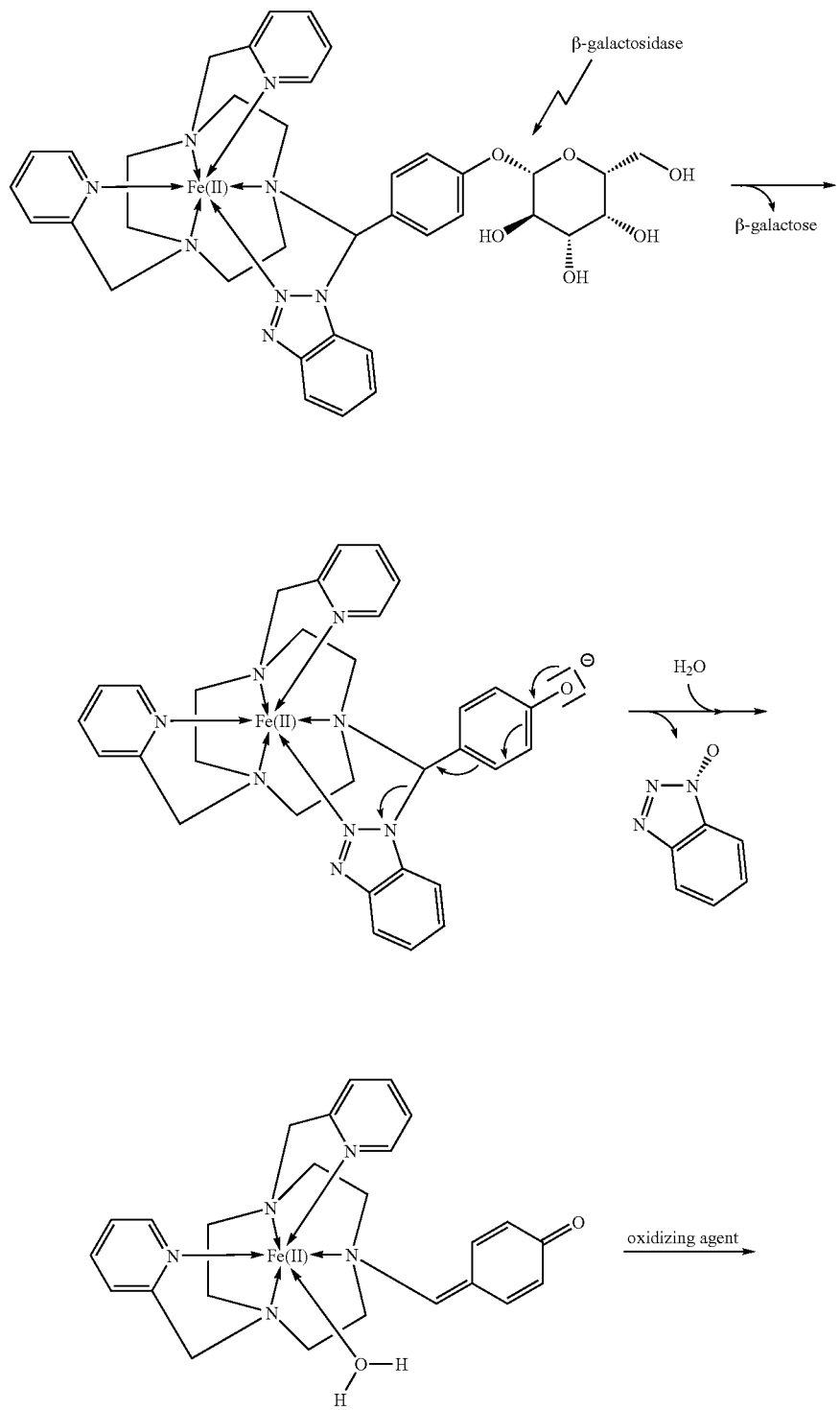

Scheme 4

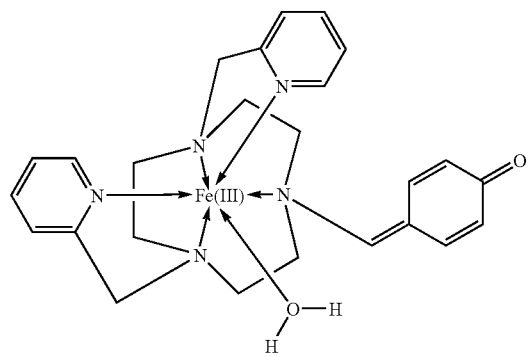

Another subject matter of the invention is a pharmaceutical composition which comprises a contrast agent according to the invention.

The invention also relates to the use of a contrast agent according to the invention in the preparation of a pharmaceutical composition intended for diagnosis by magnetic resonance imaging and to the method for diagnosis by magnetic resonance imaging of a cell or of a tissue to which a contrast agent according to the invention has been administered.

In addition, a subject matter of the invention is a pharmaceutical composition intended for the determination of the tissue distribution of β-galactosidase or of β-glucuronidase in which the contrast agent corresponds to the formula (Ia) in which $R^5$ represents an -E-$R^6$ group or a ($C_6X_4$—Y)—$R^6$ group, $R^6$ respectively representing a β-galactosyl group or a β-glucuronyl group, and the E, ($C_6X_4$—Y), $R^i$ and $R^4$ groups are as defined above.

Another subject matter of the invention is a pharmaceutical composition intended for the determination of the tissue distribution of aminopeptidases, of lipases, of transaldolases and of phosphatases in which the contrast agent corresponds to the formula (Ia) in which $R^5$ represents an -E-$R^6$ group or a ($C_6X_4$—Y)—$R^6$ group, $R^6$ representing an L-leucyl group, a —$COC_5H_{11}$ group, a group of α,β-dihydroxyacetone type

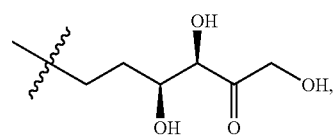

a prolyl group or a phosphoryl group, and the E, ($C_6X_4$—Y), $R^i$ and $R^4$ groups are as defined above.

Likewise, a subject matter of the invention is a pharmaceutical composition intended for the determination of the tissue distribution of L-threonine aldolase in which the contrast agent corresponds to the formula (Ib).

Preparation of a Complex of (Ia) Type in Which $R^5$ is an —O—CO—C($CH_3$)$_2$—($CH_2$)$_2$—O$R^6$ Group The preparation of a complex (Ia-1) in which $R^6$ is a galactosyl group and the other $R^i$ and $R^4$ substituents are hydrogen atoms can be carried out as illustrated by scheme 5:

Scheme 5

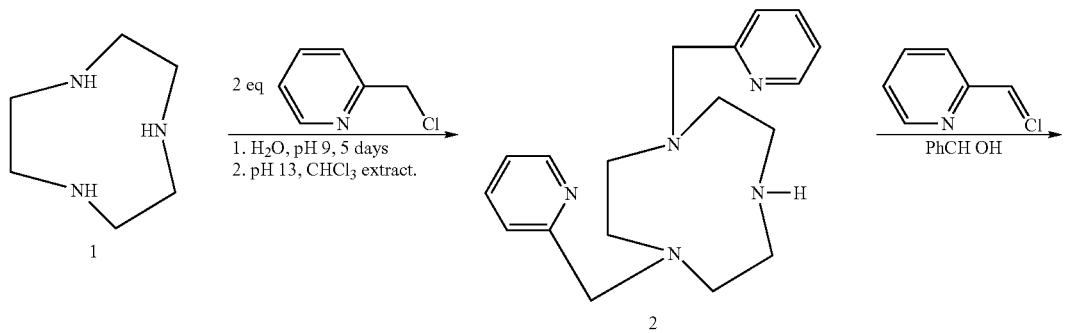

-continued
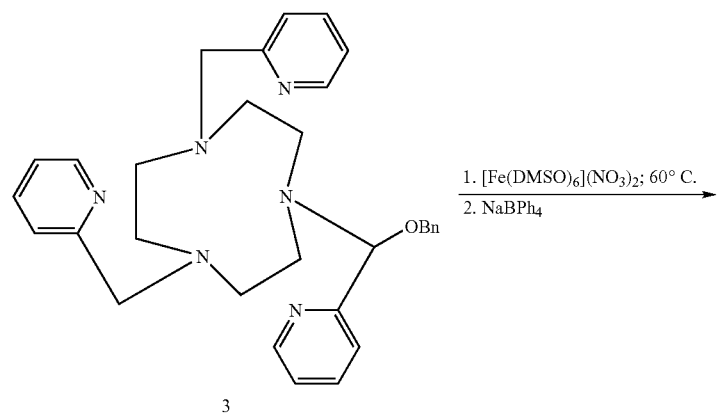
3
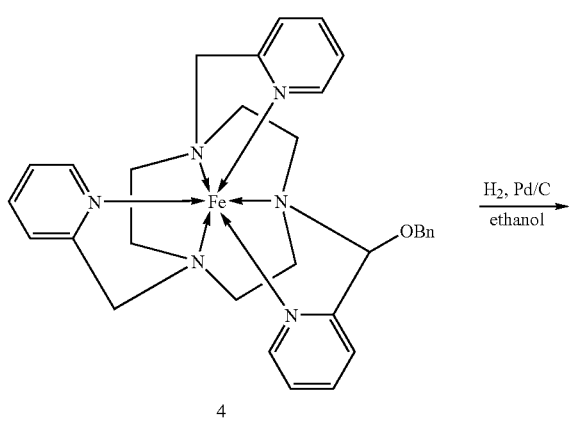
4
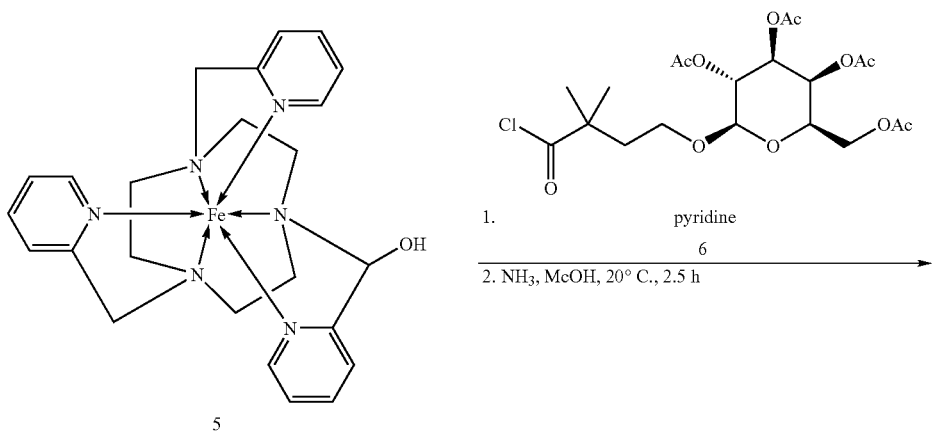
5
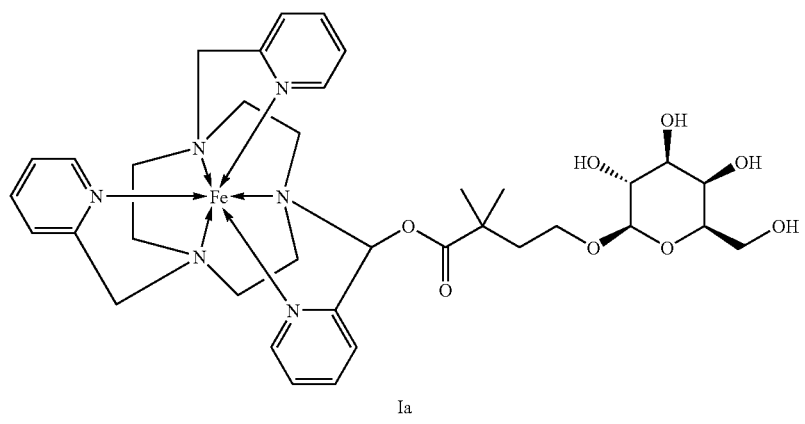
Ia

Compound (2) is prepared by reacting 1,4,7-triazacyclononane (1), available commercially, with two equivalents of chloromethylpyridine in aqueous medium at pH 9 for 3 days; at this point, the pH has fallen to 7. The pH is again adjusted to 9 and the mixture is stirred for an additional 3 days before extracting the compound (2), according to the procedure described by Spiccia et al., *Inorg. Chem.*, 1994, 33, 4663.

The compound (2) is subsequently converted to the benzylated N/O-acetal (3) by reaction with pyridine-2-carbaldehyde in benzyl alcohol in the presence of LiOH at 60° C., according to a process published for an analogous product by Ugalde-Saldivar et al. (*J. Chem. Soc. Dalton Trans.*, 2001, 3099-3107).

Subsequently, the compound (3) is converted to the iron complex (4) by reaction with [Fe(DMSO)$_6$] (NO$_3$)$_2$ at 60° C. in methanol for 30 minutes, followed by the addition of NaBPh$_4$, before cooling to 5° C. to precipitate the complex and to isolate it.

After removing the benzyl group with hydrogen in the presence of palladium-on-charcoal in ethanol, the compound (5) is obtained and is reacted with the acyl chloride (6) (see its synthesis below) in pyridine, and a complex is obtained in which the galactosyl group is in the protected form. Deprotection is carried out by the action of aqueous ammonia in methanol at 20° C. for 2.5 hours, and the desired complex of formula (Ia) is obtained.

The present invention also relates to the compound (4) of use as synthetic intermediate.

The following scheme 6 can be used to synthesize the acyl chloride (6):

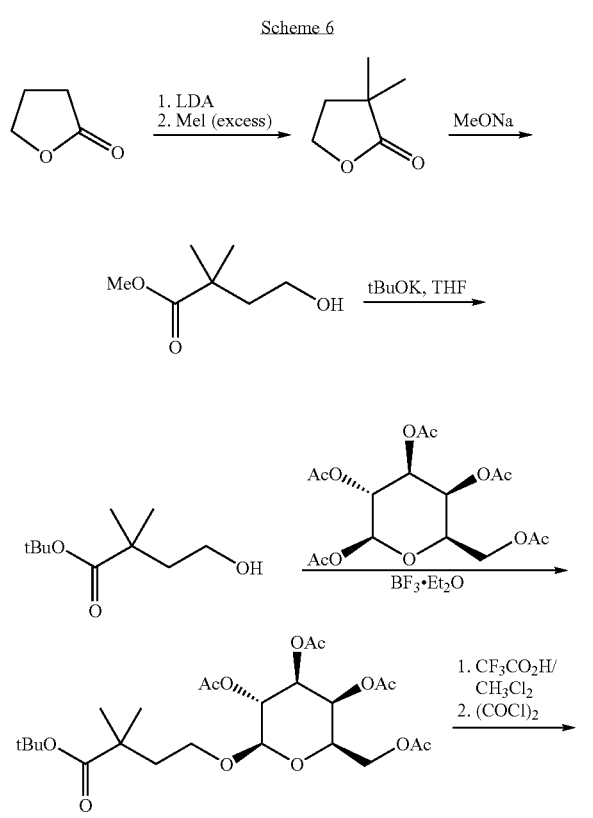

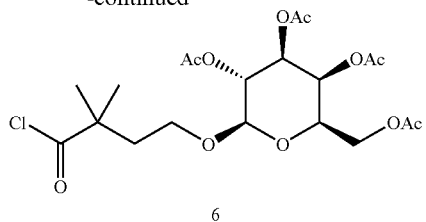

In order to obtain a complex of formula (Ia) in which the spacer is of (E2) type, the precursor analogous to the acyl chloride (6) can be synthesized according to the following scheme 7:

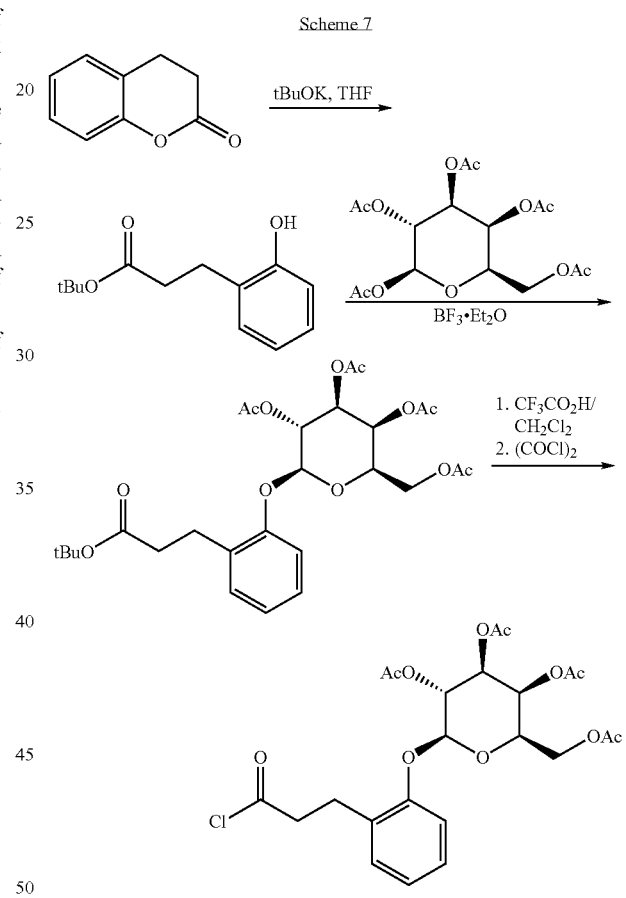

To obtain complexes of formula (Ia) in which the R$^i$ substituents are not hydrogen atoms, the preparation can be carried out in the same way using chloromethylpyridine substituted with the desired R$^i$ groups. For example, reference may be made to scheme 9 for the preparation of para-nitro-substituted chloromethylpyridine as starting material in the first stage of scheme 5.

To obtain complexes of formula (Ia) in which E-R$^6$ has the more general definition —O—CO—(CR$_{12}$)$_n$—Y—R$^6$ with R', n, Y and R$^6$ as defined above, the preparation is carried out as in scheme 5 by coupling a compound (4), hydrogenated beforehand, with an acyl chloride of formula Cl—CO—(CR$_{12}$)$_n$—Y—R$^6$ in the presence of a base. An optionally protected complex of formula (Ia) is then obtained, which can subsequently be deprotected according to conventional techniques of a person skilled in the art.

Preparation of the Complexes of (Ia) Type in Which $R^5$ is a $C_6H_4$—$OR^6$ Group
The preparation of a complex (Ia-2) in which $R^6$ is a β-galactosyl group and the other $R^i$ and $R^4$ substituents are hydrogen atoms can be carried out as illustrated by scheme 8.
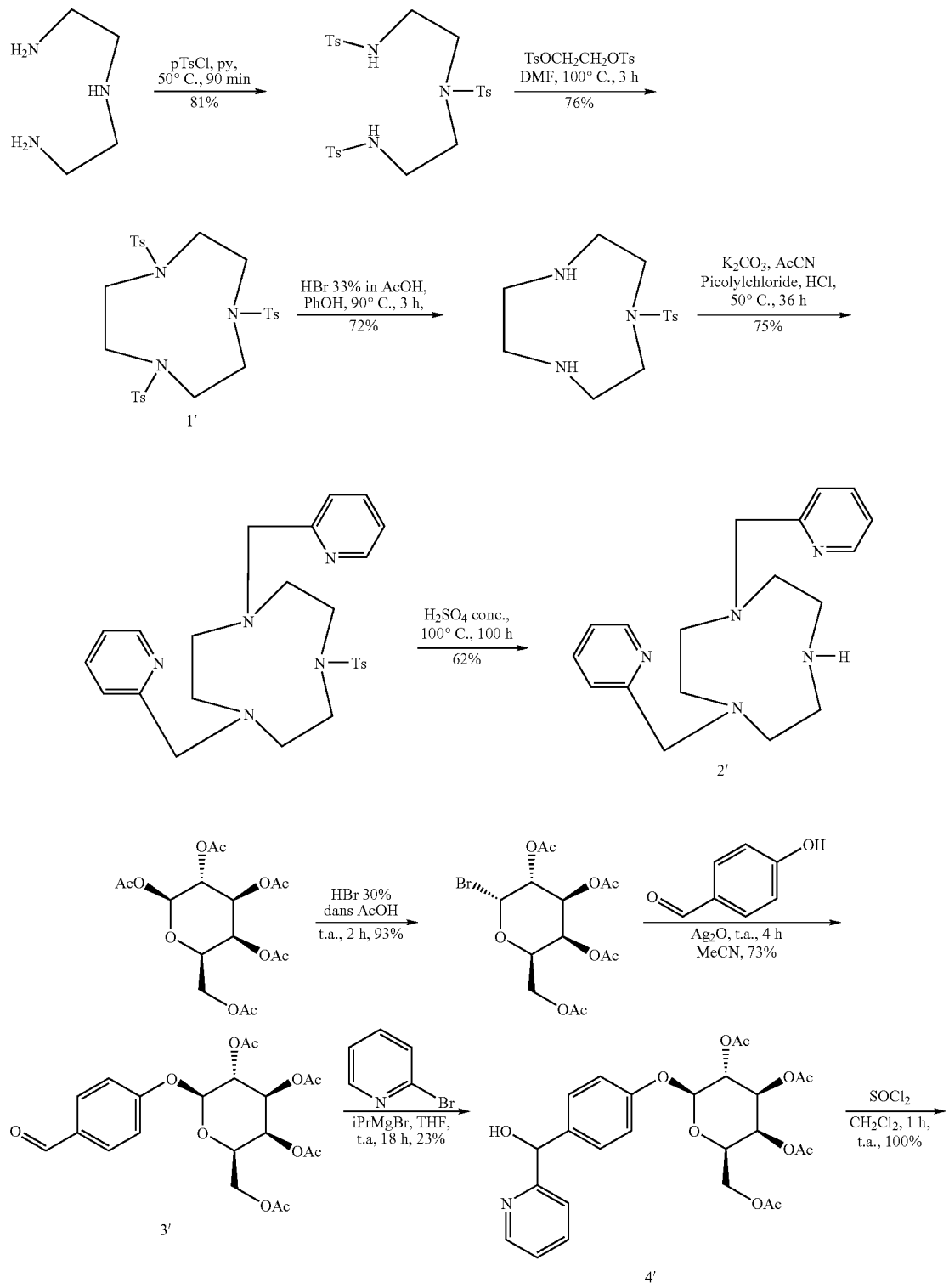

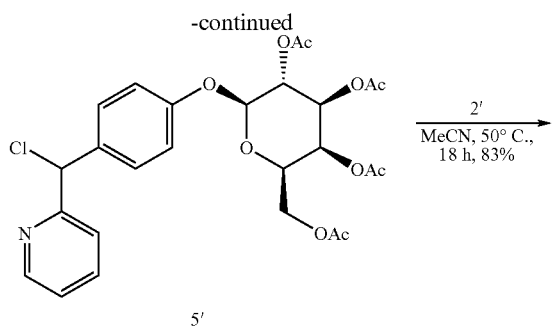

5'

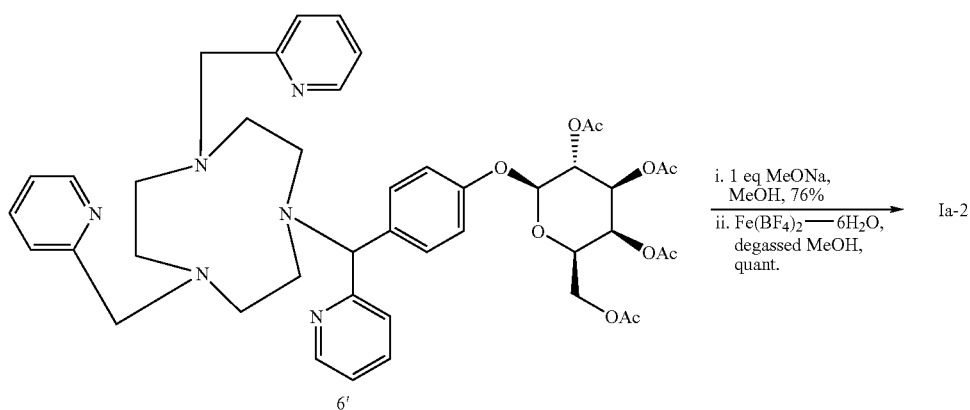

6'

The compound (2') is prepared by reacting diethylenetriamine (available commercially) with tosyl chloride. The resulting compound is treated in a first stage with MeONa and subsequently in an independent stage with ethylene glycol bistosylate to provide the product (1'). Two nitrogen atoms of (1') can be selectively deprotected by the action of hydrobromic acid in glacial acetic acid. Treatment with picolyl chloride hydrochloride introduces the two picolyl arms onto the nitrogenous macrocycle and the final tosyl group is removed by treatment in concentrated sulfuric acid at 100° C. to provide the compound (2').

The compound (3') is obtained by reacting, in the presence of silver oxide, 4-hydroxybenzaldehyde (available commercially) with 1-bromo-tetra-O-acetyl-β-D-galactopyranose, the latter being obtained by treatment of penta-O-acetyl-β-D-galactopyranose (available commercially) with hydrobromic acid in glacial acetic acid.

Subsequently, the compound (3') is treated with a mixture of one equivalent of 2-bromopyridine and of one equivalent of isopropylmagnesium bromide to produce the alcohol (4'). The latter can be converted to the chloride (5') by reaction with thionyl chloride. The compound (5') is used to alkylate the compound (2') with the help of potassium carbonate to produce the compound (6'). The latter is treated with MeONa in methanol to remove the four acetyl protective groups on the galactosyl unit. The multistage synthesis of the Ia-2 complex ends with the treatment with $Fe(BF_4)_2$ in methanol to complex the ligand with an iron(II) atom.

The preparation of the various compounds formed during this synthesis is illustrated by examples 1 to 14.

To obtain complexes of formula (Ia-2) in which the $R^i$ substituents are not hydrogen atoms, the preparation can be carried out in the same way using chloromethylpyridine substituted with the desired $R^i$ and/or $R^4$ groups. For example, reference may be made to scheme 9 for the preparation of para-nitro-substituted chloromethylpyridine as starting material in the first stage of scheme 8.

To obtain complexes of formula (Ia-2) in which E-$R^6$ has the more general definition —$C_6X_4$—Y—$R^6$ with X, Y and $R^6$ as defined above, the preparation is carried out as in scheme 8, the penta-O-acetyl-β-D-galactopyranose reactant being replaced by an acyl chloride, for the $R^6$ units corresponding to an esterase/lipase activity, and by a protected and activated amino acid, for response to the activity of proteases. For the $R^6$ unit representing an α,β-dihydroxyketone, the strategy described in the publication by E. Gonzalez-Garcia et al., Chem. Eur. J., 2003, 9, 893-899, can be applied.

To obtain complexes of formula (Ia-2) in which $R^4$ represents a methyl group, it is necessary to synthesize a derivative corresponding to the picolyl chloride introduced in the first stage of scheme 8.

Preparation of the Complexes of (Ib) Type in which $R^5$ is a Hydrogen Atom and One of the $R^i$ Substituents is a —CH(OH)CH(COOH)NH$_2$ Group A complex (Ib) in which $R^5$ is a hydrogen atom, one of the $R^i$ substituents is a —CH(OH)CH(COOH)NH$_2$ group and the remaining $R^i$ substituents are —NO$_2$ groups can be obtained from the abovementioned cyclene (1) and the reactants prepared beforehand.

A reactant (7) can be prepared according to the following reaction scheme (scheme 9). The final stage is carried out under reflux of dichloromethane.

Scheme 9
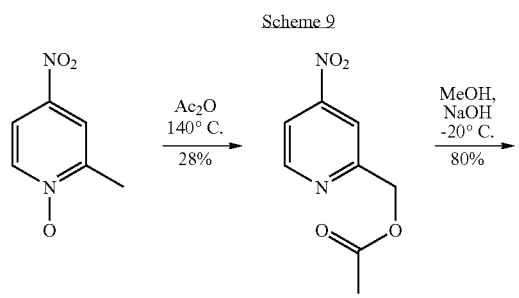
A reactant (8) can be prepared according to the following reaction scheme (scheme 10). The fourth stage is carried out by heating the starting material with selenium dioxide in dioxane for 4 days (Bishop et al., *Tetrahedron*, 2000, 4629-4638).
Scheme 10
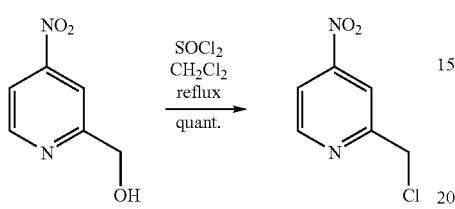
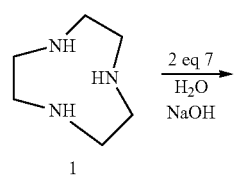
The preparation of the complex can be carried out according to the following procedure, illustrated by scheme 11:
Scheme 11
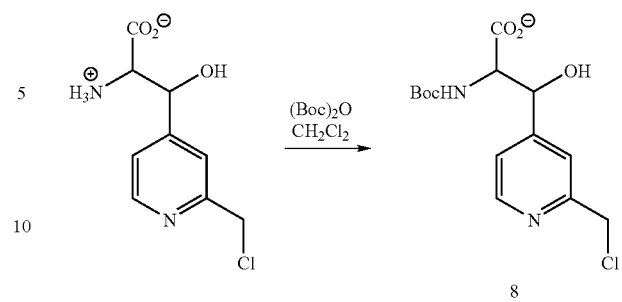
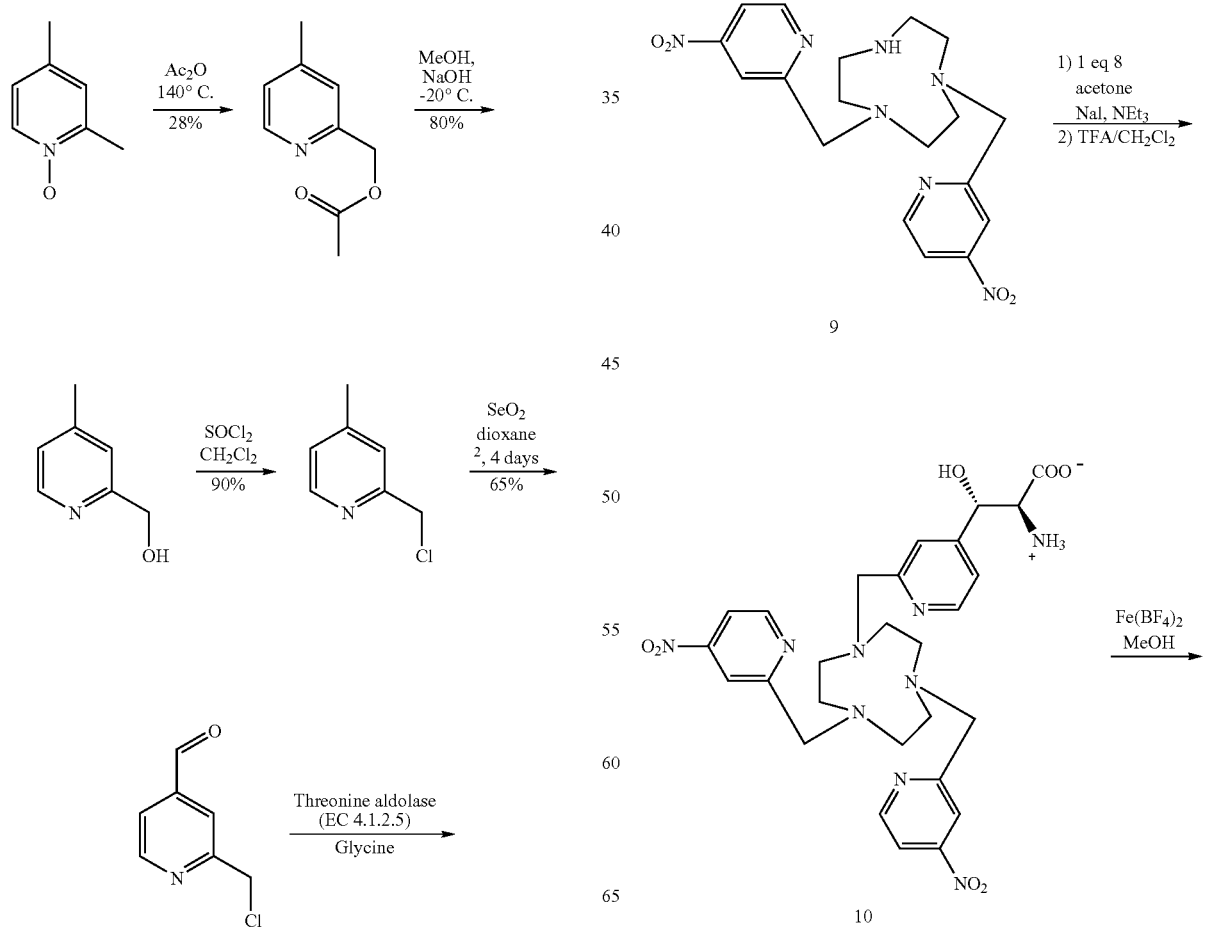

-continued

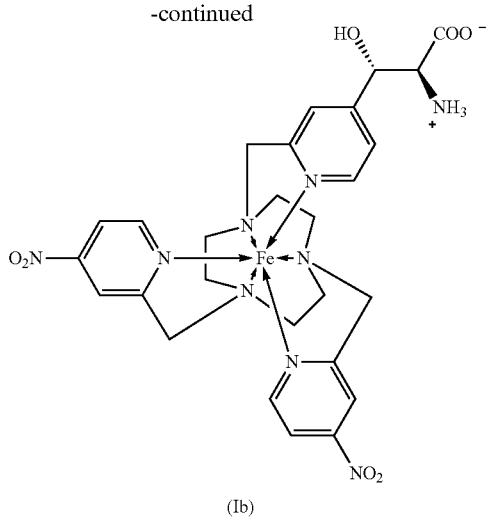

(Ib)

The preparation is carried out according to the same procedure as that described in scheme 5 to produce the compound of formula (9). Subsequently, the compound (9) is reacted with one equivalent of compound (8) in the presence of NaI and $NEt_3$ in acetone. Deprotection of the primary amine group by trifluoroacetic acid in dichloromethane results in the compound (10). The compound (10) is converted to the iron complex by the action of $Fe(BF_4)_2$ in methanol and the complex of formula (Ib) is obtained.

The present invention also relates to the compound (9), of use as synthetic intermediate.

Preparation of the Complexes of Type II

The preparation of a complex of type II in which $R^5$ is a $—C_6H_4—O-\beta$-galactosyl group, the two nitrogen atoms and the Z group together constitute a benzotriazole unit, W does not represent anything (m=0) and $R^1$, $R^2$ and $R^4$ represent hydrogen atoms can be carried out as illustrated by scheme 12.

Scheme 12

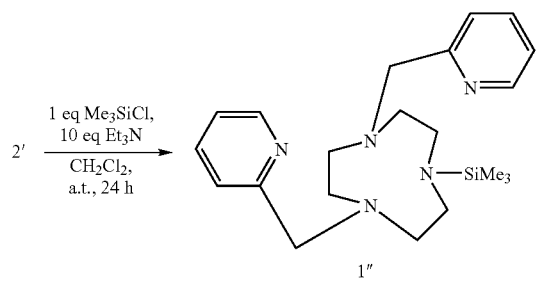

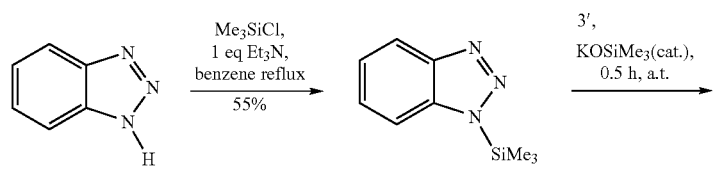

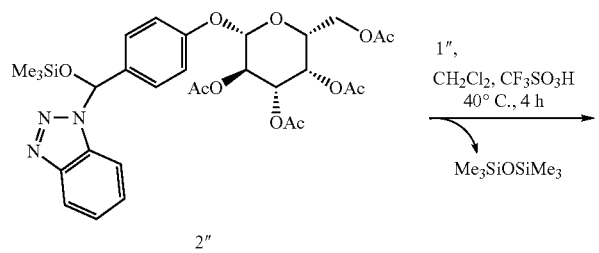

-continued

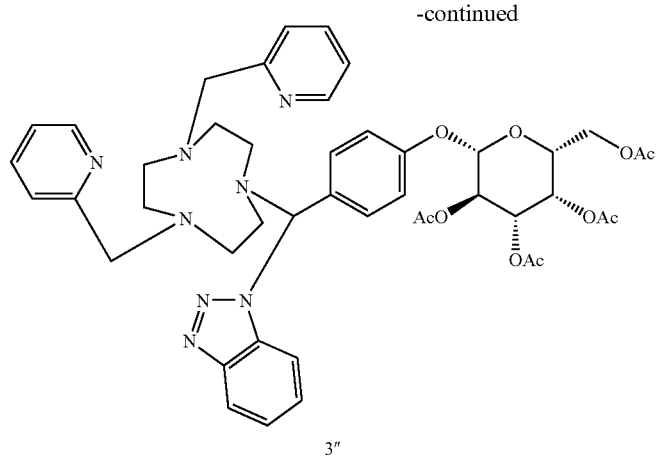

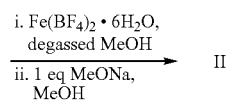

3″

The compound (1″) is obtained by reacting the product (2′), described in scheme 8, with chlorotrimethylsilane in the presence of a large excess of triethylamine, according to a procedure published for another secondary amine (P. B. Rasmussen et al., Bull. Soc. Chem. Fr., 1985, II, 62-64). After filtration, evaporation of any volatile product, redissolution in dichloromethane and filtration of the residual solids, the compound (1″) is directly introduced into the reaction with the product (2″). The latter is first of all synthesized by manufacturing 1-trimethylsilylbenzotriazole according to a procedure described in the literature (Inorg. Chem., 1989, 28, 4022-4026) and by reacting the latter with the compound (3′) described in scheme 8 according to a published procedure (A. Bourry et al., J. Heterocylic Chem., 2002, 39, 109-118).

The compounds (1″) and (2″) are converted to the compound (3″) according to a procedure described in the same publication (A. Bourry et al., J. Heterocylic Chem., 2002, 39, 109-118). The final stage consists in treating the compound (3″) with Fe(BF$_4$)$_2$ in methanol and then with MeONa in methanol, to remove the 4 acetyl protective groups on the galactosyl unit. The resulting complex II is purified by evaporation of the reaction mixture, redissolution in water and passage through a commercial column filled with reverse phase silica (C18).

The invention is described in more detail by the following examples, to which, however, it is not limited.

Examples 1 to 14 describe the preparation of the various compounds involved in the synthesis of the complexes of type Ia-2 according to scheme 8.

Example 1

Preparation of bis(p-toluenesulfonyl)ethylene glycol 19.8 g (0.3 mol) of ethylene glycol are dissolved in 150 ml of distilled pyridine and then the solution is cooled with an ice bath. p-Toluenesulfonyl chloride (123 g, 0.65 mol) is added slowly with mechanical stirring. The temperature must remain below 20° C. during the addition. When approximately 90 g have been added, stirring becomes difficult and the mixture is diluted with 200 ml of pyridine. The reaction mixture is left stirring for 2 h 30. An aqueous HCl solution (12N HCl (170 ml) in ice (500 ml)) is added. The solid formed during this addition is filtered off. This solid is dissolved in refluxing methanol (250 ml) and then the new precipitate formed after returning to ambient temperature is filtered off. Finally, the white solid obtained is dried under vacuum and the pure product is obtained (92.4 g, yield 83%).

Characteristics: $^1$H NMR (200 MHz, CDCl$_3$) δ 7.71 (d, 2H), 7.31 (d, 2H), 4.16 (s, 2H), 2.43 (s, 3H).

Example 2

Preparation of tris(p-toluenesulfonyl)diethylenetriamine 115 g (0.6 mol) of p-toluenesulfonyl chloride are dissolved in 250 ml of pyridine at ambient temperature. A solution of diethylenetriamine (21.5 ml, 0.2 mol) in pyridine (30 ml) is added dropwise. The reaction mixture is stirred at 50° C. for 90 minutes and then transferred under warm conditions to an erlenmeyer flask. After returning to ambient temperature, 200 ml of water are added. The mixture is left stirring overnight at ambient temperature and is then placed in an ice bath for 2 hours. The orange solid which then forms is filtered off and washed with cold (0° C.) 95% ethanol. After drying under vacuum at 40° C. (rotary evaporator), the desired product is obtained in the form of a light yellow solid (92 g, yield 81%).

Example 3

Preparation of the Disodium Salt of tris(p-toluenesulfonyl)diethylenetriamine

A sodium ethoxide solution is prepared by slow addition of pieces of sodium (7.5 g, 0.32 mol) to absolute ethanol (220 ml). The tris(p-toluenesulfonyl)diethylenetriamine (92.0 g, 0.16 mol) is dissolved in absolute ethanol (220 ml) and the mixture is brought to reflux. Heating is halted and the sodium ethoxide solution is added all at once. The insoluble impurities are removed by separation by settling. The solution is allowed to crystallize overnight. The crystals obtained are filtered off under argon, washed with absolute ethanol and then dried under vacuum at 100° C. The disodium salt is obtained in the form of white crystals (98.0 g, yield 98%).

Example 4

Preparation of 1,4,7-tris(p-toluenesulfonyl)-1,4,7-triazacyclononane (Compound 1′)

A solution of bis(p-toluenesulfonyl)ethylene glycol (59.5 g, 0.16 mol) in DMF (300 ml) is added dropwise, over a period of 3 hours, to a solution of the disodium salt of tris(p-toluenesulfonyl)diethylenetriamine (98 g, 0.16 mol) in DMF (950 ml) at 100° C. Heating is halted and distilled water (575 ml) is added. A precipitate is immediately formed. After filtration and drying under vacuum, the macrocyclic compound is obtained in the form of a white solid (71.8 g, yield 76%).

Characteristics:

$^1$H NMR (200 MHz, CDCl$_3$) δ 7.67 (d, 6H), 7.29 (d, 6H), 3.39 (s, 12H), 2.41 (s, 9H).

Example 5

Preparation of 1-(p-toluenesulfonyl)-1,4,7-triazacyclononane 1,4,7-Tris(p-toluenesulfonyl)-1,4,7-triazacyclononane (17.56 g, 29.7 mmol) and phenol (21 g, 223.0 mmol) are dissolved in 240 ml of a solution of HBr (33%) in glacial acetic acid. The solution is heated at 90° C. for 30 h. A solid appears after 3 h. After returning to ambient temperature, the mixture is filtered and the solid is washed with diethyl ether (2×80 ml). The hydrobromide salt is dissolved in a 1M sodium hydroxide solution until the pH is of the order of 12 units. The aqueous solution is extracted with chloroform (8×50 ml). The combined organic phases are dried over Na$_2$SO$_4$ and the solvent is evaporated under vacuum. Finally, a white solid is obtained (7.36 g, yield 88%).

Example 6

Preparation of 1-(p-toluenesulfonyl)-4,7-(pyridinyl-methyl)-1,4,7-triazacyclononane Chloropicoline hydrochloride (4.30 g, 26.20 mmol) is added to a suspension of 1-(p-toluenesulfonyl)-1,4,7-triazacyclononane (3.37 g, 11.91 mmol) and of K$_2$CO$_3$ (12 g, 86.83 mmol) in 60 ml of distilled acetonitrile. The mixture is left stirring at 50° C. under argon for 36 h. The salt obtained is filtered off and then washed with acetonitrile (2×10 ml). The solvent is evaporated under vacuum and then the product is purified by chromatography on silica gel (CH$_2$Cl$_2$/MeOH gradient from 15/1 to 5/1) to produce the pure product in the form of a yellow oil (2.98 g, yield 75%).

Characteristics:

$^1$H NMR (200 MHz, CDCl$_3$) δ 8.49 (d, 2H), 7.63 (m, 4H), 7.47 (d, 2H), 7.26 (t, 2H), 7.13 (t, 2H), 3.90 (s, 4H), 3.19 (dd, 8H), 2.80 (s, 4H), 2.40 (s, 3H);

$^{13}$C NMR (50 MHz, CDCl$_3$) δ 159.83, 148.81, 142.82, 136.23, 135.81, 129.44, 126.93, 123.06, 121.77, 63.65, 55.65, 50.73, 21.29.

Example 7

Preparation of 1,4-dipyridinylmethyl-1,4,7-triazacyclononane (Compound 2')

1-(p-Toluenesulfonyl)-4,7-(pyridinylmethyl)-1,4,7-triazacyclononane (502 mg, 1.08 mmol) is dissolved in 5 ml of concentrated H$_2$SO$_4$ under argon. The mixture is left stirring at 100° C. for 32 h. After returning to ambient temperature, the solution is cooled using an ice bath and then a 50% NaOH solution is slowly added until the pH is in the region of 12. The aqueous phase is extracted with 3×150 ml of chloroform. The organic phase is dried over Na$_2$SO$_4$ and evaporated under vacuum to produce a yellow oil (255 mg, yield 76%).

Characteristics:

$^1$H NMR (200 MHz, CDCl$_3$) δ 8.57 (d, 2H), 7.53 (t, 2H), 7.15 (dd, 4H), 3.85 (s, 4H), 3.15 (t, 4H), 2.95 (t, 4H), 2.65 (s, 4H);

$^{13}$C NMR (50 MHz, CDCl$_3$) δ 157.2, 149.29, 136.72, 122.76, 122.45, 60.81, 52.65, 49.39, 45.20.

Example 8

Preparation of tetraacetyl-α-bromogalactose

Pentaacetyl-β-galactose (10 g, 25.5 mmol) is dissolved in 25 ml of a solution of HBr (33%) in acetic acid and 5 ml of acetic anhydride. The solution is left stirring at ambient temperature for 2 hours. 200 ml of CH$_2$Cl$_2$ are added and then the solution is poured onto 150 g of ice. The organic phase is separated and the aqueous phase is extracted with 2×100 ml of CH$_2$Cl$_2$. The combined organic phases are washed with a saturated K$_2$CO$_3$ solution and then with distilled water. Drying is carried out over Na$_2$SO$_4$ and the solvent is evaporated under vacuum. The oil obtained is dissolved in the minimum amount of diethyl ether, and pentane is added to precipitate the product. The pure crystalline product is filtered off directly (9.76 g, yield 93%).

Characteristics:

$^1$H NMR (200 MHz, CDCl$_3$) δ 6.69 (d, J=3.9 Hz, 1H), 5.51 (dd, J=3.2 Hz, J=1 Hz 1H), 5.40 (dd, J=10.6 Hz, J=3.2 Hz, 1H), 5.04 (dd, J=10.6 Hz, J=3.9 Hz, 1H), 4.48 (t, J=6.5 Hz, 1H), 4.17 (m, 2H), 2.15 (s, 3H), 2.11 (s, 3H), 2.09 (s, 3H), 2.01 (s, 3H);

M.p.=85.3° C.; $[α]_{289\,nm}^{20°\,C.}$=219° (c=1, CHCl$_3$).

Example 9

Preparation of tetraacetyl-(p-formylphenoxy)-β-galactose (Compound 3')

Tetraacetyl-α-bromogalactose (4.112 g, 10 mmol) is dissolved in 100 ml of distilled acetonitrile. Ag$_2$O (10.0 g, 43 mmol) and p-hydroxybenzaldehyde (1.222 g, 10 mmol) are added. The mixture is left stirring for 4 h, the solvent is evaporated under vacuum and the resulting metal suspension is filtered through a layer of silica, ethyl acetate being used as eluent. The solvent is evaporated under vacuum and the yellow oil obtained is purified with a chromatography column on silica gel (Et$_2$O). The pure product crystallizes by slow evaporation of the solvent in the fractions comprising it. 3.04 g (yield 67%) of crystals are then obtained.

Characteristics:

$^1$H NMR (200 MHz, CDCl$_3$) δ 9.93 (s, 1H), 7.85 (d, J=8.7 Hz, 2H), 7.11 (d, J=8.7 Hz, 2H), 5.47 (m, 2H), 5.17 (m, 2H), 4.17 (m, 3H), 2.19 (s, 3H), 2.06 (s, 6H), 2.02 (s, 3H);

$^{13}$C NMR (50 MHz, CDCl$_3$) δ 190.60, 170.22, 170.07, 169.97, 169.21, 161.22, 131.73, 116.68, 98.53, 71.27, 70.60, 68.35, 66.71, 61.29, 20.56, 20.48;

M.p.=116.4° C.

Example 10

Preparation of tetraacetyl-(p-(pyridinylhydroxymethyl)phenoxy)-β-galactose (Compound 4')

2-Bromopyridine (726 mg, 440 μl, 4.6 mmol) is dissolved in 5 ml of THF at ambient temperature. Isopropylmagnesium chloride (2.3 ml, 4.6 mmol, 2M in THF) is added dropwise under argon and the mixture is left stirring for 2 hours. This solution is added to a solution of tetraacetyl-(p-formylphenoxy)-β-galactose (2.07 g, 4.6 mmol) in 3 ml of THF at ambient temperature. The mixture is left stirring for 18 h and then a saturated $NH_4Cl$ solution is slowly added. The resulting aqueous solution is extracted with ethyl acetate. The organic phase is dried over $Na_2SO_4$ and evaporated under vacuum. The crude reaction product is purified by chromatography on silica gel (ether/pentane 2/1 pure ether). A yellow solid is then obtained (600 mg, yield 25%).

Characteristics:
$^1$H NMR (200 MHz, $CDCl_3$) δ 8.57 (d, J=4.7 Hz, 1H), 7.63 (td, J=7.6 Hz, J=1.4 Hz, 1H), 7.30 (d, J=8.6 Hz, 2H), 7.21 (t, J=4.7 Hz, 1H), 7.13 (d, J=7.6 Hz, 1H), 6.97 (d, J=8.6 Hz, 2H), 5.72 (d, J=4.2 Hz, 1H), 5.43-5.47 (m, 2H), 5.19 (d, J=4.2 Hz, 1H), 5.08 (dd, J=7.9 Hz, J=4.2 Hz, 1H), 5.01 (d, J=7.9 Hz, 1H), 3.97-4.22 (m, 3H), 2.17 (s, 3H), 2.05 (s, 3H), 2.03 (s, 3H), 2.00 (s, 3H).

Example 11

Preparation of tetraacetyl-(p-(pyridinylchloromethyl)-phenoxy)-β-galactose (Compound 5')

Tetraacetyl-(p-(pyridinylhydroxymethyl)phenoxy)-β-galactose (600 mg, 1.1 mmol) is dissolved in 15 ml of $CH_2Cl_2$. $SOCl_2$ (143 mg, 88 μl, 1.2 mmol) is added dropwise and the solution is left stirring for 1 hour. The solvent is evaporated under vacuum. The product is obtained pure and quantitatively.

Characteristics:
$^1$H NMR (200 MHz, $CDCl_3$) δ 8.64 (d, J=5.2 Hz, 1H), 8.42 (t, J=7.8 Hz, 1H), 8.19 (d, J=7.8 Hz, 1H), 7.81 (t, J=6.4 Hz, 1H), 7.67 (dd, J=8.6 Hz, J=3.3, 2H), 7.11 (d, J=2.1 Hz, 1H), 7.01 (d, J=8.6 Hz, 2H), 5.44-5.51 (m, 2H), 5.12 (d, J=2.9 Hz, 1H), 5.04 (d, J=7.9 Hz, 1H), 4.01-4.20 (m, 3H), 2.17 (s, 3H), 2.06 (s, 3H), 2.03 (s, 3H), 2.00 (s, 3H).

Example 12

Preparation of 1,4-dipyridinylmethyl-7-(pyridinyl(p-(tetraacetyl-β-galacto)phenyl)methyl)-1,4,7-triazacyclononane (Compound 6')

1,4-Dipyridinylmethyl-1,4,7-triazacyclononane (168 mg, 0.5 mmol), tetraacetyl-(p-(pyridinylchloromethyl)phenoxy)-β-galactose (356 mg, 0.6 mmol) and $K_2CO_3$ (approximately 1.5 g, 11 mmol) are mixed in 10 ml of acetonitrile. The resulting suspension is left stirring overnight at 50° C. under argon. After returning to ambient temperature, the precipitate is filtered off and washed with 2×5 ml of acetonitrile. The solvent is evaporated from the filtrate and a yellow oil is obtained which is purified by chromatography on silica gel ($CH_2Cl_2$/MeOH 10/1 to $CH_2Cl_2$/MeOH/$NH_4OH$ 4/1/0.1) so as to obtain the pure product (327 mg, yield 74%).

Characteristics:
$^1$H NMR (200 MHz, $CDCl_3$) δ 8.48 (t, J=4.4 Hz, 3H), 7.63 (td, J=7.6 Hz, J=1.6 Hz, 3H), 7.36 (d, J=8.6 Hz, 2H), 7.13 (m, 3H), 6.89 (d, J=8.6 Hz, 2H), 5.42 (m, 2H), 5.06 (dd, J=7.9 Hz, J=4.2 Hz, 1H), 4.98 (d, J=7.9 Hz, 1H), 4.78 (s, 1H), 3.97-4.22 (m, 3H), 3.79 (s, 4H), 2.96 (s, 4H), 2.84 (d, J=8.6 Hz, 4H), 2.16 (s, 3H), 2.03 (s, 3H), 2.02 (s, 3H), 2.00 (s, 3H).

$^{13}$C NMR (50 MHz, $CDCl_3$) δ 179.29 (C), 179.21 (C), 170.09 (C), 169.33 (C), 162.98 (C), 160.40 (C), 155.82 (C), 148.88 (CH), 137.19 (C), 136.42 (CH), 136.24 (CH), 129.79 (CH), 123.16 (CH), 122.64 (CH), 121.80 (CH), 116.73 (CH), 99.50 (CH), 70.84 (CH), 68.61 (CH), 66.82 (CH), 64.63 ($CH_2$), 61.26 ($CH_2$), 55.78 ($CH_2$), 55.52 ($CH_2$), 53.99 ($CH_2$), 20.62 ($CH_3$).

Example 13

Preparation of 1,4-dipyridinylmethyl-7-(pyridinyl(p-(β-galacto)phenyl)methyl)-1,4,7-triazacyclononane 1,4-Dipyridinylmethyl-7-(pyridinyl(p-(tetraacetyl-β-galacto)phenyl)methyl)-1,4,7-triazacyclononane (124 mg, 0.15 mmol) is dissolved in 2 ml of methanol. Sodium methoxide (9 mg, 0.15 mmol) is added. The reaction mixture is left stirring under argon for 4 h, after which period the substrate is completely consumed according to LCMS. The solvent is evaporated under vacuum, then $CHCl_3$ (2 ml) is added and a precipitate appears. The solution is filtered and the solid is washed with chloroform. The solvent is evaporated under vacuum and the product is obtained in the form of a yellow oil (78 mg, yield 79%).

Example 14

Preparation of [Fe(1,4-dipyridinylmethyl-7-(pyridinyl(p-(β-galacto)phenyl)methyl)-1,4,7-triazacyclononane)]$^2$ $(BF_4)^-$ A solution of iron(II) bis(tetrafluoroborate) hexahydrate (68 mg, 0.18 mmol) in degassed methanol (1 ml) is added via a hollow needle to a solution of 1,4-dipyridinylmethyl-7-(pyridinyl(p-(β-galacto)phenyl)methyl)-1,4,7-triazacyclononane (139 mg, 0.21 mmol) in 0.5 ml of degassed methanol under argon. A dark-brown color instantaneously appears. The mixture is left stirring at ambient temperature for 10 minutes and then the solvent is evaporated under vacuum. The crude reaction product is purified by two successive filtrations on a $C^{18}$ reverse phase silica column using water as eluent to produce the pure complex in the form of a yellow solid after lyophilization (103 mg, yield 65%).

What is claimed is:

1. A contrast agent for magnetic resonance imaging comprising a chelating ligand and a transition metal ion, said ligand carrying a substituent capable of reacting chemically or biochemically with a target substance while bringing about a change in the spin state, and comprising:

a) either the formula (I)

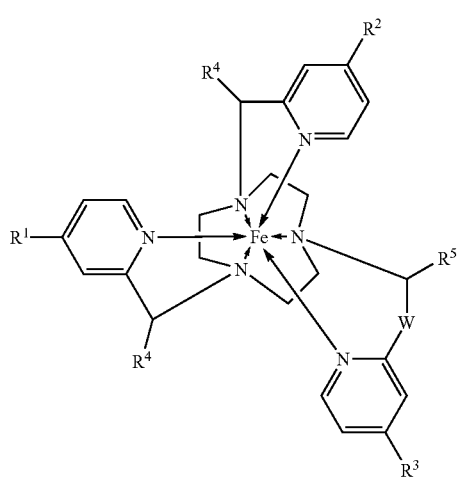

b) or the formula (II)

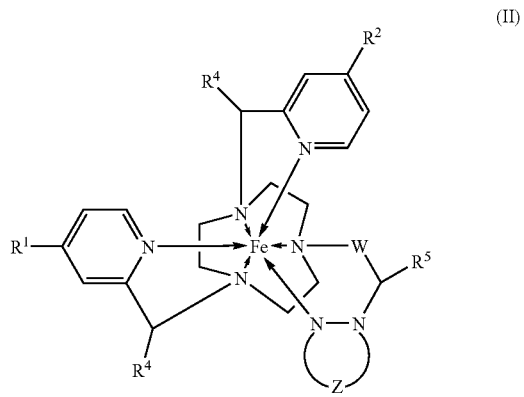

in which:
R⁴ represents a hydrogen atom or a linear of branched alkyl group of 1 to 4 carbon atoms or an aryl radical;
W represents a —(CH$_2$)$_m$— group, m being equal to 0 or to 1;
R⁵ represents a hydrogen atom, or represents a -E-R⁶ or —C$_6$X$_4$—Y—R⁶ group, in which E and C$_6$X$_4$—Y are spacer groups and R⁶ represents a β-galactosyl group, a β-glucoronyl group, a L-leucyl group, a —COC$_5$H$_{11}$ group, a group of α,β-dihydroxyacetone type, a prolyl group or a phosphoryl group, X is an electron-withdrawing group, at least one X of C$_6$X$_4$—Y being selected from the group consisting of methyl, chloro, fluoro, nitro, methoxy, carboxy and acetamido groups; E is an —O—CO—(CR'$_2$)$_n$—Y— group in which the R' groups represent, independently of one another, a hydrogen atom or a methyl group or two R' groups carried by two neighboring carbon atoms together form a 5- or 6-membered aliphatic or aromatic ring carried by the two neighboring carbon atoms; n is an integer equal to 3 or 4; Y is a heteroatom chosen from an oxygen atom, a nitrogen atom or a sulphur atom, it being understood that:
i) when R⁵ represents a -E-R⁶ or —C$_6$X$_4$—Y—R⁶ group (complexes Ia), the substituents R¹ to R³, denoted by R$^i$, represent, independently of one another, a hydrogen atom or a group chosen in order to adjust the properties of solubility and of dispersibility in biological media and of magnetic moment of the complex, it also being possible for one of the R$^i$ groups to represent a group capable of undergoing electronic modification of the neighboring pyridyl group by reaction with the target substance;
ii) when R⁵ represents a hydrogen atom (complexes Ib), one of the R$^i$ groups represents a group —CH(OH)CH(COOH)NH$_2$, it being possible for the remaining R$^i$ groups to represent, independently of one another, a hydrogen atom, a halogen atom or a group chosen from the —COOR⁷ groups in which R⁷ is an alkyl group having from 1 to 4 carbon atoms, a —NO$_2$ group or a —CHO group;

in which:
R¹ and R², denoted by R$^i$, represent, independently of one another, a hydrogen atom or a group chosen in order to adjust the properties of solubility and of dispersibility in biological media and of magnetic moment of the complex;
R⁴ and W are as defined above;
R⁵ represents a group (—C$_6$X$_4$—Y—R⁶) in which X is an electron-withdrawing group, Y is a heteroatom chosen from an oxygen atom, a nitrogen atom or a sulfur atom, and R⁶ represents a β-galactosyl group, a β-glucuronyl group, a L-leucyl group, a —COC$_5$H$_{11}$ group, a group of α,β-dihydroxyacetone type, a prolyl group or a phosphoryl group;
Z is a divalent group which forms, with the two nitrogen atoms which carry it, an aromatic benzotriazole, triazole, tetrazole or pyrazole ring, it being possible for said aromatic ring to carry an NO$_2$ substituent.

2. The contrast agent of formula (II) as claimed in claim 1, wherein:
R⁶ represents a β-galactosyl group, a β-glucuronyl group, an L-prolyl group, an L-leucyl group, a —COC$_5$H$_{11}$ group, a group of α,β-dihydroxyketone type

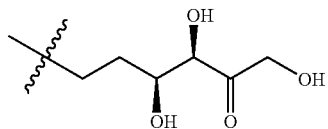 [SMILES: *CC[C@H](O)[C@@H](O)C(=O)CO]

or a phosphoryl group;
the X groups represent, independently of one another, a hydrogen atom, a fluorine atom or an NO$_2$ group.

3. The contrast agent as claimed in claim 1 corresponding to the formula (Ia), wherein the R$^i$ groups represent, independently of one another, a hydrogen atom, an electron-withdrawing group chosen from the —COOR⁷ groups in which R⁷ represents an alkyl group having from 1 to 4 carbon atoms, the —NO$_2$ group, a halogen atom and the —CH$_2$—COO⁻ group, or else one of the three R$^i$ groups represents a —CH(OH)CH(COOH)NH$_2$ group, the remaining R$^i$ groups then being as defined above.

4. The contrast agent as claimed in claim 3 corresponding to the formula Ia, wherein R⁵ corresponds to the formula -E-R⁶ in which E is a spacer group capable of self-collapsing in the event of cleavage of the E-R⁶ bond and R⁶ is a group capable of reacting with a chemical compound or a biochemical compound, triggering a sequence of cleavages resulting in the elimination of the pyridine-2-carbaldehyde.

5. The contrast agent as claimed in claim 4, wherein:

R$^6$ represents a group capable of undergoing cleavage by a glycosidase, or an aminoacyl group capable of undergoing cleavage by an aminopeptidase, or an acyl group capable of undergoing cleavage by an esterase or a lipase, or a group capable of undergoing a retrograde aldol reaction with a natural aldolase, or a group capable of undergoing conversion by a phosphatase, for example a phosphoryl group.

6. The contrast agent as claimed in claim 5, wherein R$^6$ represents a β-galactosyl group, a β-glucuronyl group, an L-prolyl group, an L-leucyl group, a —COC$_5$H$_{11}$ group, a group of α,β-dihydroxyketone type

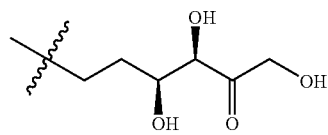 [SMILES: *CC[C@H](O)[C@@H](O)C(=O)CO]

or a phosphoryl group.

7. The contrast agent as claimed in claim 5, wherein the 5- or 6-membered aromatic ring is chosen from the phenyl, pyridyl, pyrimidinyl, pyrazinyl, indolyle, indazolyl, furyl and thienyl groups, wherein said aromatic groups are optionally substituted with one or more substituents chosen from the methyl, chloro, fluoro, nitro, methoxy, carboxyl and acetamido groups, and the 5- or 6-membered aliphatic ring is a cyclohexyl group or a cyclopentyl group.

8. The contrast agent as claimed in claim 5, wherein E corresponds to one of the following formulae:

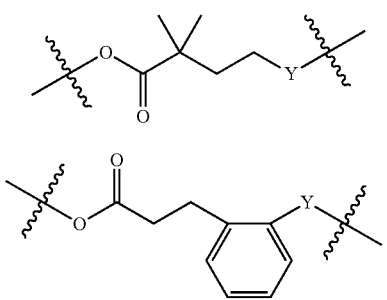

9. The contrast agent as claimed in claim 1 corresponding to the formula Ia, wherein:

R$^5$ corresponds to the formula —C$_6$X$_4$—Y—R$^6$ in which (C$_6$X$_4$—Y) is a spacer group capable of self-collapsing in the event of cleavage of the —(C$_6$X$_4$—Y)—R$^6$ bond, and R$^6$ is a group capable of reacting with a chemical compound or a biochemical compound while triggering a sequence of cleavages bringing about the elimination of a quinonemethide.

10. The contrast agent as claimed in claim 9, wherein:

Y is a heteroatom chosen from an oxygen atom, a nitrogen atom or a sulfur atom;

X is an electron-withdrawing group, and

R$^6$ represents a group capable of undergoing cleavage by glycosidase, or an aminoacyl group capable of undergoing cleavage by an aminopeptidase, or an acyl group capable of undergoing cleavage by an esterase or a lipase, or a group capable of undergoing a retrograde aldol reaction with a natural aldolase, or a group capable of undergoing conversion by a phosphatase, for example a phosphoryl group.

11. The contrast agent as claimed in claim 10, wherein:

R$^6$ represents a β-galactosyl group, a β-glucuronyl group, an L-prolyl group, an L-leucyl group, a —COC$_5$H$_{11}$ group, a group of α,β-dihydroxyketone type

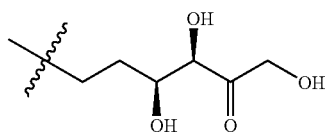 [SMILES: *CC[C@H](O)[C@@H](O)C(=O)CO]

or a phosphoryl group;

the X groups represent, independently of one another, a hydrogen atom, a fluorine atom or an NO$_2$ group.

12. The contrast agent as claimed in claim 9, wherein (C$_6$X$_4$—Y) corresponds to one of the following formulae:

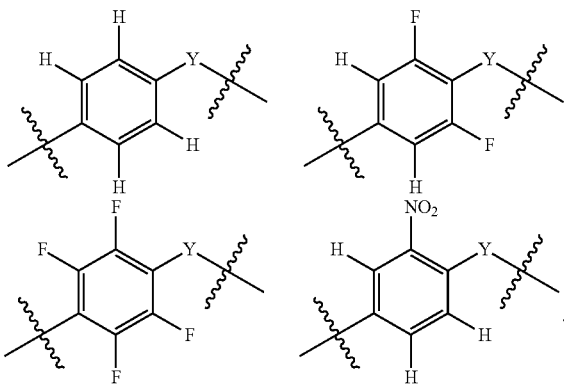

13. The contrast agent as claimed in claim 1 corresponding to the formula Ib, wherein one of the three R$^i$ groups represents a —CH(OH)CH(COOH)NH$_2$ group and the remaining R$^i$ groups represent, independently of one another, a hydrogen atom, a halogen atom or a group chosen from the —COOR$^7$ groups in which R$^7$ can represent an alkyl group having from 1 to 4 carbon atoms, the —NO$_2$ group or the —CHO group.

14. The contrast agent as claimed in claim 1 corresponding to the formula (II), wherein (C$_6$X$_4$—Y) corresponds to one of the following formulae:

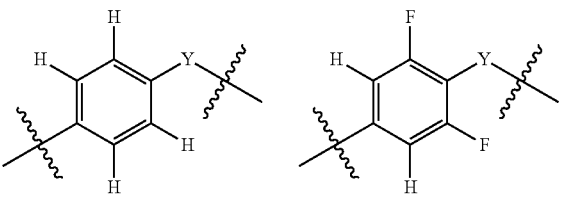

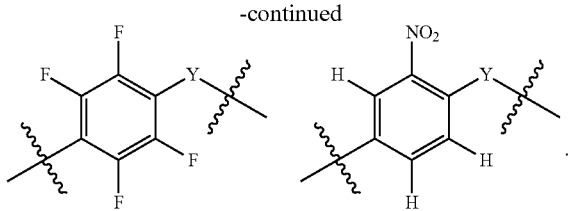

15. A pharmaceutical composition comprising a contrast agent as claimed in claim 1 in combination with a pharmaceutically acceptable excipient.

16. The pharmaceutical composition as claimed in claim 15, wherein the contrast agent is as defined in claim 4, $R^6$ respectively representing a β-galactosyl group or a β-glucuronyl group.

17. The pharmaceutical composition as claimed in claim 15, intended for the determination of the tissue distribution of aminopeptidases, of lipases, of transaldolases and of phosphatases, wherein the contrast agent is as defined in claim 4, $R^6$ representing an L-leucyl group, a —$COC_5H_{11}$ group, a group of α,β-dihydroxyacetone type

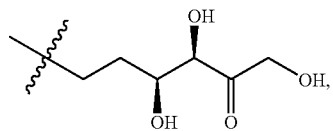

a prolyl group or a phosphoryl group.

18. The pharmaceutical composition as claimed in claim 15, intended for the determination of the tissue distribution of L-threonine aldolase, wherein the contrast agent is as defined in claim 13.

* * * * *